(12) United States Patent
Hoffmann et al.

(10) Patent No.: US 11,865,324 B2
(45) Date of Patent: Jan. 9, 2024

(54) INJECTION DEVICES

(71) Applicant: RepliCEL Life Sciences Inc., Vancouver (CA)

(72) Inventors: Rolf Hoffmann, Freiburg (DE); Martin Hohlrieder, Feldkrich (AT)

(73) Assignee: RepliCel Life Sciences Inc., Vancouver (CA)

(*) Notice: Subject to any disclaimer, the term of this patent is extended or adjusted under 35 U.S.C. 154(b) by 0 days.

(21) Appl. No.: 17/328,951

(22) Filed: May 24, 2021

(65) Prior Publication Data

US 2021/0346611 A1 Nov. 11, 2021

Related U.S. Application Data

(62) Division of application No. 15/501,171, filed as application No. PCT/US2015/044110 on Aug. 6, 2015, now Pat. No. 11,045,612.

(60) Provisional application No. 62/198,655, filed on Jul. 29, 2015, provisional application No. 62/034,140, filed on Aug. 6, 2014.

(51) Int. Cl.
*A61M 5/44* (2006.01)
*A61M 5/32* (2006.01)
(Continued)

(52) U.S. Cl.
CPC ................ *A61M 5/44* (2013.01); *A61M 5/19* (2013.01); *A61M 5/20* (2013.01); *A61M 5/24* (2013.01);
(Continued)

(58) Field of Classification Search
CPC ............ A61M 5/44; A61M 5/19; A61M 5/20; A61M 5/24; A61M 5/31515; A61M 5/31546; A61M 5/3202; A61M 5/3298; A61M 5/422; A61M 5/46; A61M 2005/2411; A61M 2005/247; A61M 2005/3126; A61M 2005/31588; A61M 2202/09; A61M 2205/13; A61M 2205/3327; A61M 2205/3344; A61M 2205/3368; A61M 2205/3379; A61M 2205/3569; A61M 2205/3606; A61M 2205/3673; A61M 2205/50; A61M 2205/505; A61M 2205/52; A61M 2205/581; A61M 2205/583; A61M 2205/587; A61M 2205/6054; A61M 2205/6072; A61M 2205/8206
See application file for complete search history.

(56) References Cited

U.S. PATENT DOCUMENTS

| 2014/0012229 A1* | 1/2014 | Bokelman | A61M 5/2033 604/154 |
| 2015/0209505 A1* | 7/2015 | Hanson | A61M 5/1454 604/135 |
| 2016/0175408 A1* | 6/2016 | Chang | A61K 38/4893 604/173 |

* cited by examiner

*Primary Examiner* — Dung T Ulsh
(74) *Attorney, Agent, or Firm* — BioMed IP PLLC

(57) ABSTRACT

The invention relates to an injection device which includes a handle and a guard which together enclose a movable cartridge which can contain liquid material to be injected, and further enclose a movable injector that includes a needle, the needle being attached to a housing where the housing is attached to the cartridge, the device also including a delivery mechanism whereby the needle is moved from a retracted to an extended position, and independently the volume of the chamber may be adjusted to expel the contents thereof through the needle and into a subject in need thereof. The injection device may be communicatively connected to a control unit so as to provide a dermal injection system.

2 Claims, 15 Drawing Sheets

(51) Int. Cl.
  *A61M 5/42* (2006.01)
  *A61M 5/46* (2006.01)
  *A61M 5/24* (2006.01)
  *A61M 5/315* (2006.01)
  *A61M 5/19* (2006.01)
  *A61M 5/20* (2006.01)
  *A61M 5/31* (2006.01)

(52) U.S. Cl.
  CPC .... *A61M 5/31515* (2013.01); *A61M 5/31546* (2013.01); *A61M 5/3202* (2013.01); *A61M 5/3298* (2013.01); *A61M 5/422* (2013.01); *A61M 5/46* (2013.01); *A61M 2005/247* (2013.01); *A61M 2005/2411* (2013.01); *A61M 2005/3126* (2013.01); *A61M 2005/31588* (2013.01); *A61M 2202/09* (2013.01); *A61M 2205/13* (2013.01); *A61M 2205/3327* (2013.01); *A61M 2205/3344* (2013.01); *A61M 2205/3368* (2013.01); *A61M 2205/3379* (2013.01); *A61M 2205/3569* (2013.01); *A61M 2205/3606* (2013.01); *A61M 2205/3673* (2013.01); *A61M 2205/50* (2013.01); *A61M 2205/505* (2013.01); *A61M 2205/52* (2013.01); *A61M 2205/581* (2013.01); *A61M 2205/583* (2013.01); *A61M 2205/587* (2013.01); *A61M 2205/6054* (2013.01); *A61M 2205/6072* (2013.01); *A61M 2205/8206* (2013.01); *A61M 2209/086* (2013.01)

INJECTION DEVICES

CROSS-REFERENCE TO RELATED APPLICATIONS

This application is a Divisional of U.S. patent application Ser. No. 15/501,171, filed Feb. 1, 2017, which is a national phase application under 35 U.S.C. § of International Application No. PCT/US2015/044110, filed Aug. 6, 2015, which claims the benefit under 35 U.S.C. § 119(e) of U.S. Provisional Patent Application No. 62/034,140 filed Aug. 6, 2014, and U.S. Provisional Patent Application No. 62/198,655 filed Jul. 29, 2015, which applications are incorporated herein by reference in their entireties.

FIELD OF THE INVENTION

The present invention relates generally to injection devices, and more specifically to devices which are suitable for injecting, delivering or otherwise administering a variety of substances, including cells, into tissue.

BACKGROUND

Humans have many different tissue layers, including skin, mucosa, subcutis, fascia, muscle, nerves, and joints. Some of these layers are themselves formed from multiple layers of distinct tissue. For example, human skin comprises several different layers. The epidermis is the outer skin layer with a thickness of about 30 to 2,000 microns. The dermis is located beneath the epidermis with a thickness of about 500 to 1,500 microns. The subcutis is located beneath the dermis with a thickness of about 500 to 30,000 microns.

It is sometimes desirable to inject a substance into a subject with more precision than provided by use of a typical syringe. For example, in a human being, it may be desirable to deliver a substance very precisely within just one distinct tissue layer. In certain applications, it is desirable to specifically deliver substances such as cells to specific locations within the skin.

There is therefore a need for means that allow that substances such as cells are injected precisely into a desired physiological tissue and not elsewhere, e.g., a nearby tissue. As one particular example, in the field of biological hair research there is a need for the accurate application of so called "dermal sheath cup" cells ("DSC") which have potential for hair follicle regenerating. Similar demands exist concerning further injection applications. For example, an injection within the skin during cosmetic or aesthetic treatment requires further distinct means for the injection. A further application concerns an injection into muscle tissue, joints, fascia, fat tissue, cartilage, submucosal tissues, or tendons. Such applications are often necessary after injuries which occur during sports or exercises.

There is a need to administer substances to tissue and distinct layers of tissue from the outside in a simple and reliable way. The application of substances (e.g., liquids, biologics, or cell suspensions) within the dermis, epidermis or subcutis as well as muscle tissue layers or tendons requires a skillful handling by a medical doctor. In addition, the application of such substances can involve distinct requirements. For example, with respect to cells, there is a need to deliver them as near to the respective tissue layer which resembles the physiological tissue layer of these cells in situ as possible. Secondly, there is also a need to apply the cells in a very careful way. Some cell types, such as stem cells or freshly prepared primary cells, are sensitive to pressure which arises during the application. Such pressure occurs, for example, when cells are delivered via a narrow cannula which results in a high compression of the cells. Such a compression and the resulting shear stress which acts on the cells are harmful. The consequence of this can be that cells are severely damaged and probably even lose their viability.

It is possible to apply cells to the scalp of a subject with a standard syringe having a needle of a distinct size and length. This has however the disadvantage that it is not possible to apply the cells in a constant manner since the needle is shifted each time the injection site is changed. Accordingly, the angle between the injection needle and the scalp surface is not constant between. Further, the injection depth will very likely vary during the different injections, since there is no measure or control over how deep the injection is if it is conducted with a standard syringe having an injection needle which is only guided by hand.

WO 02/083216 AI describes a device and a method for the intradermal injection of substances. The device allows injections of a defined depth of penetration which allows for intradermal delivery, wherein the needle is injected perpendicular to the plane of the skin.

WO 94/23777 AI describes an intradermal injection device which allows a subcutaneous injection and the optional application of a vacuum.

However, none of the devices of the prior art achieves the delivery of liquid substances, such as cells, without the application of pressure or shear-stress. Furthermore, none of the devices of the prior art achieves the application of liquid substances, such as cells, in a reliable way which ensures that the application occurs at the optimal physiologic site.

The application of cells to, for example, the scalp of a subject, requires distinct requirements as outlined above. Further, it is necessary that the cells are applied within a single layer or region and in a distributed manner. Accordingly, it is desired that the cells are not injected in punctual form but preferably in a more dispersed way.

There is a need for a device which overcomes the problems as described above and which allows for the delivery of substances, in particular biological substances such as cells, in a careful manner and at the desired physiological site in a reliable and reproducible way. This underlying technical problem is solved with the injection device as described herein, which provides for liquid substances and cell suspensions to be administered to tissue in a careful and gentle way, where the delivery is targeted to the desired physiologic tissue layer.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

Briefly stated, the invention relates to a dermal injector system, an injection device, and uses thereof to deliver substances to specific tissue in a uniform and reproducible manner.

For example, the present disclosure provides a dermal injector system comprising:
  a. an injection device, the injection device having an injector arranged for mechanical communication with at least one needle, a cartridge arranged to hold at least one injectable material through the at least one needle, an electromechanical drive device arranged to advance and retract the at least one needle, and communication interface; and
  b. a control unit, the control unit communicatively connectable to the injection device through the communication interface, the control unit including a processor, a memory arranged to store processor-executable instructions, and a plurality of sensors, a first sensor arranged to pass information associated with a position of the at least one needle, and a second sensor arranged to pass information associated with the cartridge.

Optionally, the injection device may be fitted with a plurality of needles, such as 4, 9, 16 or 25. Also optionally, the injection device may incorporate a cooling feature which will contact tissue adjacent to the tissue that will receive the injection, and cool the contacted and adjacent tissue, so that the injection is less painful to the patient. Preferably, the injection device incorporates both a plurality of needles and a cooling feature, each as described in detail herein. For example, in one embodiment, the at least one needle of the dermal injector system includes a needle array. In another embodiment, the cartridge includes a form of Digital Rights Management, e.g., an identifiable tag or marker. Examples include RFID tags (and alternatives such as HP Memory Spot and RuBee (IEEE 1902.1)), ink markings, QR codes and barcodes. The Digital Rights Management (e.g., identifiable tag or marker) can be arranged to store information about material in the cartridge, where such information may include, for example, the composition to be delivered, manufacturer, date of manufacture, lot number and/or serial number). In yet another embodiment, the dermal injector system further comprises a cooling tip coupleable to the injection device, where the cooling tip is optionally arranged to provide temperature information to the control unit and/or where the cooling tip optionally comprises a Peltier element. In still another embodiment, the control unit is arranged to receive user input, such as user input that directs needle depth and/or material volume. The user input may also specify needle injection speed and/or needle withdrawal speed.

In addition, the present disclosure provides an injection device. In one aspect the injection device includes a handle and a guard which together enclose a movable cartridge which can contain liquid material to be injected. The handle and guard also enclose a movable injector that includes a needle, the needle being attached to a housing where the housing is attached to the cartridge. The device may also include a delivery mechanism including a motor whereby the needle is moved from a retracted (protected, non-exposed) position to an extended position where it can be used to inject a substance into a subject. Independent from the movement of the needle, the volume of the chamber may be adjusted to expel the contents thereof through the needle and into a subject in need thereof.

In one embodiment, the present disclosure provides an injection device (10) as set forth in embodiment 1) as well as optional features thereof as set forth in embodiments 2-8):
  1) An injection device (10) having a proximal end which may facilitate holding or gripping the device and a distal end for introducing a liquid substance into the body of a subject, the injection device comprising:
      a) an injector (14) comprising at least one needle (24) and a housing (26) for the at least one needle;
      b) a cartridge (16) comprising at least one chamber (20) to hold the liquid substance, and a plunger (48) which moves within the chamber to change a volume of the chamber; and
      c) a delivery mechanism (40) to independently move the plunger and the needle toward the distal end of the device (10), the delivery mechanism comprising a distal drive (42) that is movable relative to the proximal end of the device, a proximal drive (44) that is stationary relative to the proximal end of the device and a threaded rod (46) that joins the proximal and distal drives and the plunger.
  2) The device (10) of embodiment 1 further comprising a guard (12) at the distal end of the device, the guard (12) having an opening through which the needle may extend.
  3) The device (10) of embodiment 1 wherein a distal end of the cartridge fits inside a proximal end of the housing.
  4) The device (10) of embodiment 1 wherein the distal drive (42) and the proximal drive (44) are adjacent to one another when the needle is in a retracted position.
  5) The device (10) of embodiment 1 wherein the distal drive (42) and the proximal drive (44) are separated from one another when the needle is in an extended position.
  6) The device (10) of any of embodiments 1-5 having more than one needle (24). Within certain embodiments the device (10) has more than 2, 3, 4, 5, 6, 7, 8, 9, 10, 11, 12, 13, 14, 15, 16, 17, 18, 19, 20, 21, 22, 23, 24, or 25 needles (24). Within further embodiments the needles can have a gauge of 18, 19, 20, 21, 22, 23, 24, 25, 26, or 27.
  7) The device (10) of any of embodiments 1-5 wherein all needles (24) are configured to penetrate simultaneously into the body of the subject.
  8) The device (10) of any of embodiments 1-7 wherein the injection depth of the injection needle (24) is in a range from preferably 0.5 mm to 5 cm, preferably 0.5 mm to 4 cm, preferably 0.5 mm to 3 cm, preferably 0.5 mm to 2 cm, preferably 0.5 mm to 1 cm, preferably 0.5 mm to 5.5 mm, preferably from 1.5 mm to 4.0 mm, more preferably from 2.0 mm to 3.5 mm, most preferably 3.4 mm.

As yet another example, the present disclosure provides a non-transitory computer-readable storage medium whose stored contents configure a computing system to perform a method, the method comprising:
  a. communicatively coupling an injection device to a control unit, the control unit having a processor arranged to execute instructions stored in the non-transitory computer-readable storage medium;
  b. receiving first user input at the control unit, the first user input directed to a depth of a needle of the injection device during an injection;
  c. receiving second user input at the control unit, the second user input directed to a volume of material delivered through the needle during the injection;
  d. receiving third user input at the control unit, the third user input directed to a speed of the needle during the injection; and
  e. receiving an indication at the control unit that the injection was performed.

Optionally, the method also comprises receiving temperature information associated with a cooling tip coupled to the injection device during the injection. Also optionally, the method comprises providing at least one audible output or at least one visual output associated with a status of the injection. In addition, the method optionally may comprise providing at least one audible output or at least one visual output directing performance of the injection by a clinician. Furthermore, the method may optionally also comprise accumulating in the control unit data indicating how many injections have been performed. And also, the method may further include receiving at the control unit information identifying a material delivered to a patient during the injection. Any one or more of these options may be combined to characterize the non-transitory computer-readable storage medium whose stored contents configure a computing system to perform a method as set forth herein.

In another example, the present disclosure provides various methods of using an injector comprising multiple needles, such as a dermal injector as disclosed herein. Thus, in one embodiment, the present disclosure provides a method of delivering cells into tissue, the method comprising placing the cells into a dermal injector as disclosed herein and then injecting the cells from the device and into the tissue. In another embodiment, the present disclosure provides a method of delivering hyaluronic acid or other filler into tissue, the method comprising placing the hyaluronic acid or other filler into a dermal injector as disclosed herein, and then injecting the hyaluronic acid or other filler into the tissue. In yet another embodiment, the present disclosure provides a method of dermal treatment comprising injecting a material into tissue of a patient, the injecting being performed with a dermal injector as described herein.

For example, in one embodiment the present disclosure provides a method comprising:
a) selecting a first exterior surface of skin of a patient, the first surface comprising a surface area and a first average temperature;
b) cooling the first surface to a second average temperature;
c) penetrating the first surface with a plurality of needles, the plurality of needles extending from the first surface by a uniform distance into the patient; and
d) withdrawing the plurality of needles from the patient while also ejecting a material out of the needles and into the patient.

The details of one or more embodiments of the device and methods of the present disclosure are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, the drawings, and the claims.

For the purpose of illustration of the present invention, the present invention is shown in illustrative form, it being understood however, that the invention is not limited to the precise form shown in the figures or examples.

BRIEF DESCRIPTION OF THE DRAWINGS

Features of the present disclosure, its nature and various advantages will be apparent from the accompanying drawings and the following detailed description of various embodiments.

Figure 1:
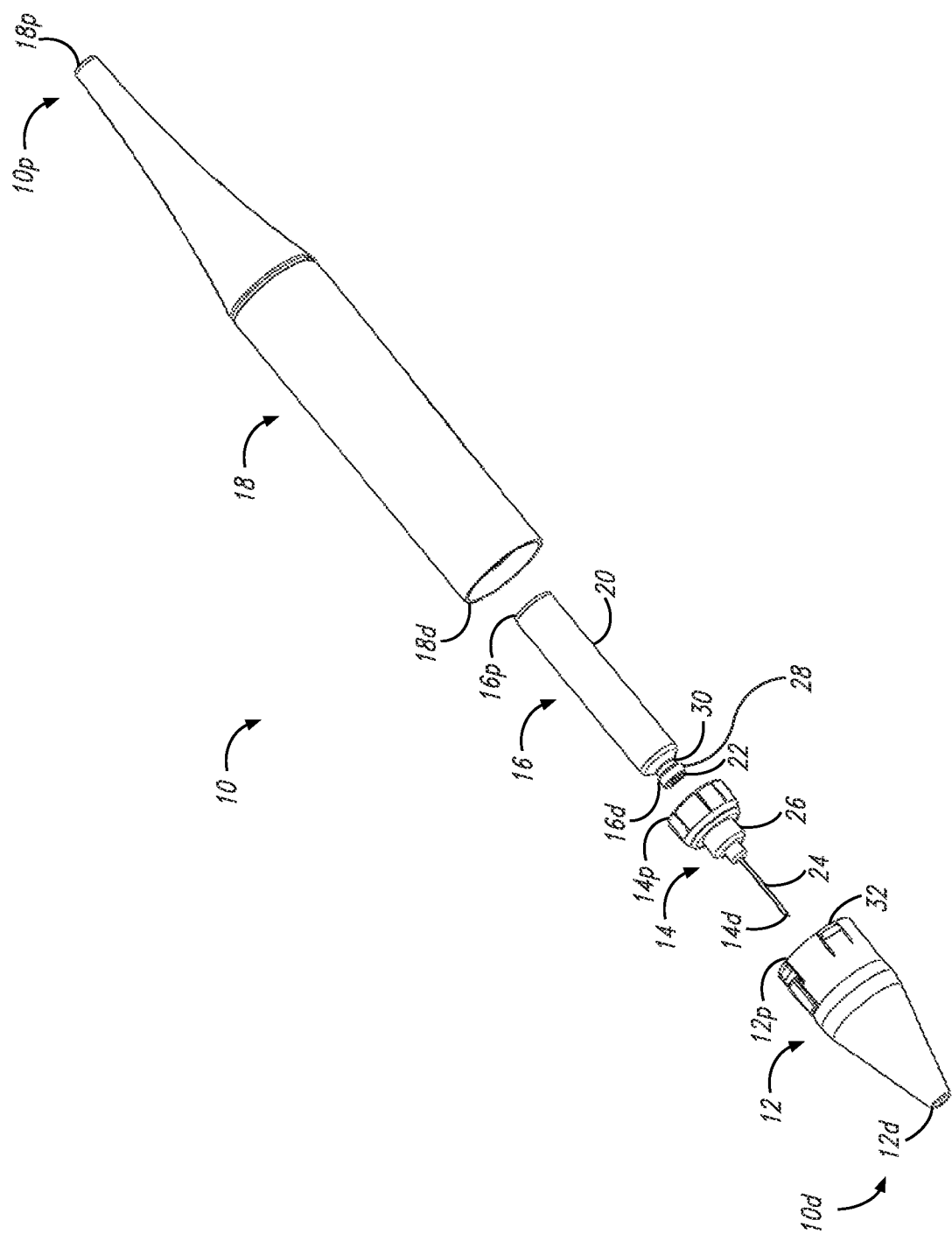
FIG. 1 shows a perspective view of a preferred embodiment of the injection device, wherein the device is shown in an exploded view to illustrate various parts of the device, including an optional guard and an injector with a single needle.

Corresponding reference numerals indicate corresponding parts throughout the drawings. The injection device (10) of the present invention has a distal end (where the needle is) and a proximal end (where the end of the handle is). For the injection device, the distal end will be denoted by reference 10*d* while the proximal end will be denoted by 10*p*. This same convention, i.e., "d" for distal and "p" for proximal following an element number, may be used for any of the elements identified herein.

DETAILED DESCRIPTION OF THE INVENTION

The present invention may be understood more readily by reference to the following detailed description of the preferred embodiments of the invention. It is to be understood that the terminology used herein is for the purpose of describing specific embodiments only and is not intended to be limiting. It is further to be understood that unless specifically defined herein, the terminology used herein is to be given its traditional meaning as known in the relevant art. Any headings used within this document are only being utilized to expedite its review by the reader, and should not be construed as limiting the invention or claims in any manner.

The present disclosure provides an injection device that is wired or wirelessly coupled to a controller unit, which together provide for a dermal injector. The injection device, which is also sometimes referred to as the hand-piece, holds the material to be injected and also comprises one or more needles through which the material passes when it is injected into a subject.

In one embodiment, the present disclosure provides an injection device which allows for the precise and targeted delivering of cells, as one example of a substance, into a specific location of a subject, e.g., in dermal tissue layers. As discussed in further detail below, the injection device is not limited to the delivery of material to only dermal tissue, however that is one useful application of the device and so the device comprising the injection device and a controller unit may be referred to herein as a dermal injector. The dermal injector of the present disclosure provides an improved level of control and precision for injecting material into specific tissue, e.g., into intradermal (dermis), subcutaneous (fat) or intramuscular injections. The injector may be used to introduce therapeutic cells into a patient, however it may also be used for administration of non-cellular material, including broad applications in dermatological procedures requiring injections of specific volumes of material at specific depths including cellular products, fillers, hyaluronic acids, fat and collagen injections.

In one embodiment, the dermal injector comprises one or more of: (a) a digital control device having an optionally integrated or separate and distinct touch-screen control which allows the operator to input desired operation parameters; (b) optionally the control screen allows the operator the ability to select both injection depth and material volume to be delivered using the digital touch-screen and associated programming, (c) a Peltier element for cooling, where this element may be removable from the injection device in order to facilitate sterilization, (d) the option to exchange one needle head for a different needle head, i.e., interchangeable needle heads, (e) a plurality of needle heads from which an appropriate needle head may be selected for the procedure to be performed, where different needle heads will have different needle configurations and/or a different number of needles and/or different sizes of needles and/or will cover a different surface area, etc., (f) pre-filled disposable cartridges, and (g) a high-powered light that shines on the region of the patient to receive the injection. These and other features of the device are described in more detail herein.

The dermal injector of the present disclosure provides numerous benefits compared to single needle syringes. For example, by exchanging heads, a variety of injectable substances having different viscosity, shear response, etc., may be delivered. With the appropriate head, the device enables broad, shallow injections for the treatment of fine wrinkles. The device increases precision and ease of application compared to single needle syringes, as well as providing for improved control and delivery. The device incorporates a comfortable grip for ease of use. The needles head, having an array of needles, provides for increased surface area coverage per application. In optional embodiments, all of the needles in the head are distributed over a maximum area of 2 $cm^2$, or 1.5 $cm^2$, or 1 $cm^2$, or 0.8 $cm^2$. In one embodiment, the maximum area of penetration by the array of needles is 1 $cm^2$. This increased coverage, relative to the coverage afforded by a single needle injection, affords quicker procedure times. The presence of a skin cooling feature, such as a Peltier element, as part of the injection device reduces and perhaps eliminates the need to use a local anesthetic to obviate the pain associated with an injection. The controlled injection will reduce the amount of pain and bruising that can accompany an injection, especially an injection that is not performed optimally by the clinician. Overall, the device of the present disclosure provides for more reproducible injections between treatments and improved consistency of results.

The injection device of the present disclosure is able to deliver substances into specific layers of the skin while controlling for depth, volume, flow rate and shear stress. These controllable features importantly allow for deposition of injectable materials in 3 dimensions (depth of injection and area of injection. By improving the conditions of substance delivery compared to currently available devices, the device of the present disclosure improves the chances of success in the treatment of the subject. In addition, the device may comprise a mechanism for temporary freezing or cooling of the skin in the area that receives the injection, which removes the need for an anesthetic and decreases procedure time. Thus, the device of the present disclosure provides significant improvements over current syringe-type devices where the needle depth and angle are not controlled and are often, if not always, accompanied by the use of an anesthetic.

An embodiment of the injection device of the present invention is shown in expanded perspective view in FIG. 1. Thus, in FIG. 1, the device 10 has a distal end 10d and a proximal end 10p. The device 10 is shown to comprise four components, which when listed from the distal end 10d of the device toward the proximal end 10p of the device are: a guard 12 having a distal end 12d and a proximal end 12p; an injector 14 having a distal end 14d and a proximal end 14p; a cartridge 16 having a distal end 16d and a proximal end 16p; and a handle 18 having a distal end 18d and a proximal end 18p. In actual operation, the proximal end 12p of the guard 12 and the distal end 18d of the handle 18 fit together, such that the injector 14 and the cartridge 16 fit inside the combined guard/handle construct. The handle may also be referred to as the hand-piece, as may the combination of the handle, the cartridge and the injector, optionally with the guard.

As mentioned previously, the present invention relates to the provision of an injection device which allows for the precise and targeted delivery of a liquid, e.g., a suspension of cells. In the present device, that liquid is held within and delivered from the cartridge 16. More specifically, the liquid is held in a chamber 20 located at the proximal end 16p of the cartridge 16, and delivered through an opening 22 at the distal end 16d of the cartridge 16.

As the liquid leaves the opening 22 of the cartridge 16, it passes into the injector 14, and more specifically the proximal end 14p of the injector 14. The injector 14 comprises a needle 24 at the distal end 14d of the injector 14, and a housing 26 at the proximal end 14p of the injector 14. The needle 24 is preferably permanently attached to, e.g., mounted on or into, the housing 26. The housing 26 serves several functions. For example, it holds the needle in proper alignment within the device. The proximal end 26p of the housing 26 provides a recess into which the distal end of the cartridge securely fits. Various mechanism may be used to fixedly seat the distal end 16*d* of the cartridge 16 in fluid communication with the housing 26. For example, the distal end 16*d* of the cartridge 16 may comprise a head 28 and a neck 30, where the neck is of smaller cross-sectional distance than is the head, and the head is optionally of smaller cross-sectional distance than is the chamber 20. The inside of the housing 26 may have a complementary shape to the head 28 and neck 30 configuration of the cartridge, e.g., the inside of the housing 26 may have an elastomeric gasket (not shown in FIG. 1) which can expand in cross-section to allow the head 28 to pass through the gasket, but after the head has passed through the gasket, the gasket contracts to its resting size which fits snugly around the neck 30 of the cartridge. An alternative seating arrangement is that the distal end of the cartridge 16 contains threads which screw into corresponding threads located inside the housing 26. As yet another option, a Luer lock mechanism may be used to hold the distal end 16*d* inside the housing 26.

While the interior (not shown) of the injector housing 26 is suited to accept the distal end 16*d* of the cartridge 16, the exterior of the housing 26, and in particular the proximal end 14*p* of the injector 14 is suited to fit within and fixedly seat within the proximal end 12*p* of the guard 12. One mechanism to hold the injector housing within the guard is shown in more detail in FIG. 2, and so discussion of that mechanism will be deferred until FIG. 2 is discussed.

The guard 12 effectively protects the needle 24 from coming into unwanted contact with the environment. The present disclosure provides that the needle 24 may extend out through the distal end 12*d* of the guard 12 in order to expose the needle and thereby allow the needle to be injected into a subject. As will be discussed later, the guard 12 may also assist in holding the injection device in proper orientation vis-à-vis the subject receiving the injection of liquid from the chamber. As also will be discussed later, the guard 12 may incorporate a cooling unit, so that when the guard contacts the skin, the contacted skin is cooled. As indicated by FIG. 1, when the guard 12 is mated to the handle 18, the needle 24 is completed covered and encased. However, as will be shown in other embodiments of the invention, the guard 12 need not fully encase the needle head in order to provide protection to the user against accidental contact with the needle(s).

The handle 18 includes a distal end 18*d* which may be fixedly but reversibly joined to the proximal end 12*p* of the guard 12. To achieve this function, the guard 12 is shown with various catches 32 which are complementary in shape and design to recesses (not shown) located on the inner wall (not shown) of the distal end 18*d* of the handle 18. Alternatively, the proximal end 12*p* of the guard 12 may have threads that could be screwed into complementary sized and shaped grooves located on the interior of the distal end 18*d* of the handle 18. While the design shown in FIG. 1 envisions that the proximal end 12*p* of the guard 12 fits within the distal end 18*d* of the handle 18, alternative arrangements may be employed to hold the guard in a secure connection with the handle 18. For example, the exterior surface of the distal end 18*d* of the handle 18 might have catches that fit inside the proximal end 12*p* of the guard 12. As another option, the guard 12 may connect to the side of the handle 18 and then extend in the distal direction until the guard 12 at least partially encloses the needle 24. In one embodiment the guard is removable from the handle, but can be attached by frictional forces to the handle. In one embodiment, the injection device will not inject any material into a subject unless the guard is attached to the handle.

Figure 2:
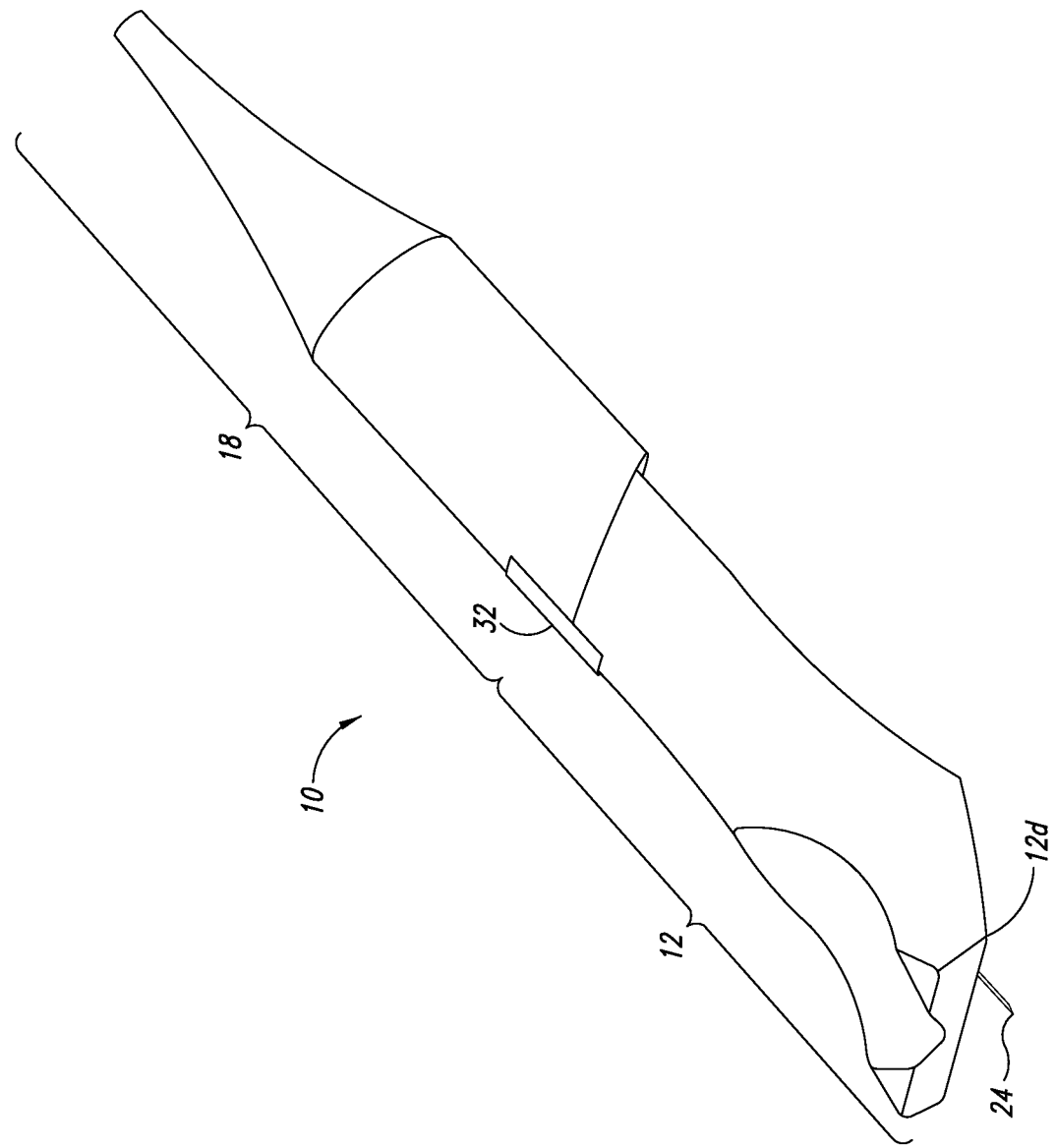
FIG. 2 shows a perspective view of a preferred embodiment of the injection device, wherein the injection needle is in its extended position.

FIG. 2 is a perspective view of an injection device of the present invention when it is ready for use. In FIG. 2, the device 10 is shown having a guard 12 and a handle 18, where the handle 18 and the guard 12 are secured together. In order to separate the guard 12 from the handle 18, a latch may be manipulated, which allows release of the guard 12 from the handle 18. The needle 24 can be seen extending from the distal end 12*d* of the guard 12. However, other than the needle, no other part of the injector 14 is visible. Likewise, the cartridge 16 resides inside the device 10 and cannot be seen in FIG. 2. The distal end 12*d* of the guard 12 as shown in FIG. 2 has been shaped into a flat surface, where this flat surface can rest on the skin of the subject that will receive the injection. The dimensions of the guard, in combination with the size and location of the needle, provide for a pre-determined depth of penetration of the needle into the skin of the subject. In other words, when the distal end 12*d* of the guard 12 is placed on the skin of the subject that will receive the injection, the depth of the injection is controlled because the needle will only extend a pre-determined distance from the distal surface of the guard. The device of the present invention has an alternative configuration to that shown in FIG. 2, namely, where the needle is in a retracted state, wholly inside of the guard.

Figure 3:
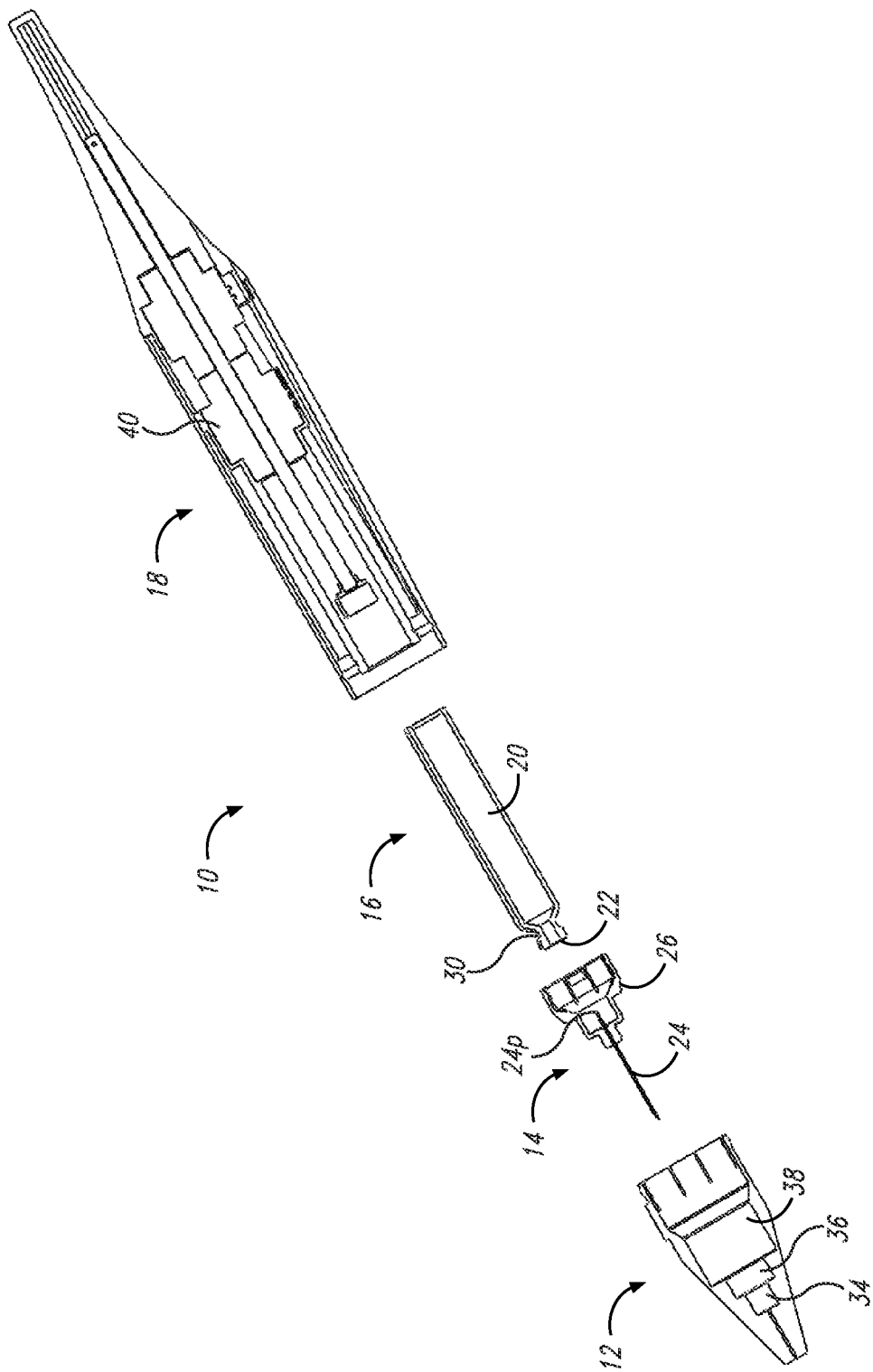
FIG. 3 shows an exploded cross-sectional view of a preferred embodiment of the injection device in longitudinal section with transparent view of the inside, in analogy to the perspective view of FIG. 1.

FIG. 3 provides an exploded cross-sectional view that corresponds to the perspective view of FIG. 1. In FIG. 3, the guard 12 is seen to have three connecting chambers: a distal chamber 34 which is smaller in cross sectional distance than the adjacent middle chamber 36, which in turn is smaller in cross sectional distance than the adjacent proximal chamber 38. These three chambers are complementary in shape and size to the housing 26 of the injector 14. Due to this complementary shape and size, the housing 26 fits within and is secured in place inside the guard chambers 34, 36 and 38. The diminishing cross-sectional distances of the chambers as viewed from the proximal to the distal ends of the guard effectively provide a block to any further movement of the injector 14 in the distal direction.

FIG. 3 also shows that the needle 24 has a proximal end 24*p* that extends into the housing 26. When the cartridge 16 is fitted inside of the injector 14, the proximal end 24*p* of the needle 24 will extend into the neck 30 of the cartridge 16. If the opening 22 of the cartridge 16 is covered with a membrane or other seal that can be pierced by the needle end 24*p*, then the liquid contents of the chamber 20 can be ejected from the cartridge through the needle 24.

FIG. 3 also shows a delivery mechanism 40 located within the handle 18. This mechanism 40 is used to move the needle from a protected configuration wholly inside the guard, to an exposed configuration where the needle extends through the distal end of the guard. This mechanism also causes the contents of the chamber 20 to be injected into the subject. The mechanism 40 is more fully explained by reference to FIGS. 5, 6 and 7, which show the disposition of the mechanism at various stages of operation.

Figure 4:
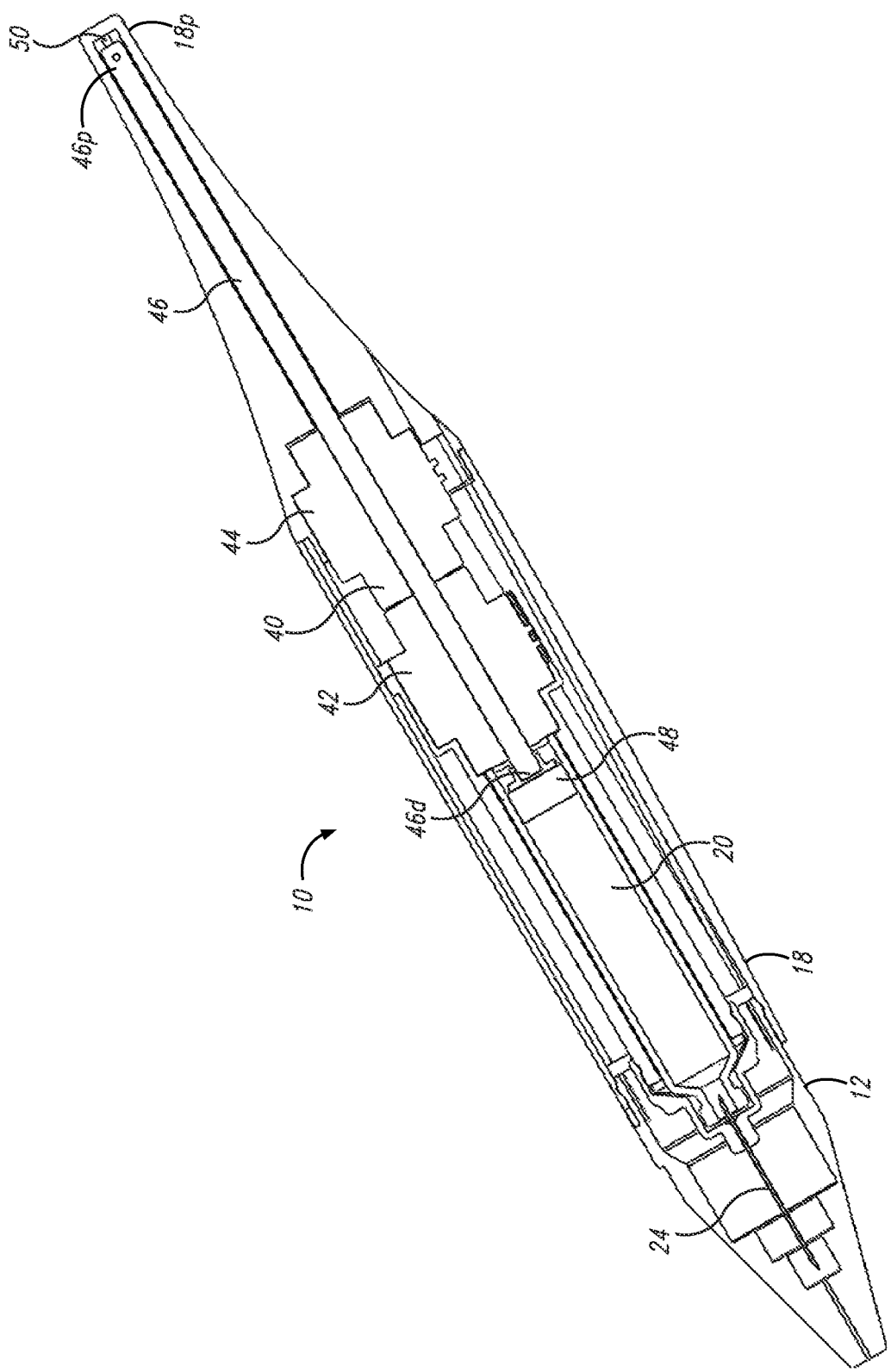
FIG. 4 shows a cross-sectional view of a preferred embodiment of the injection device, where the needle is in the retracted position and the chamber is full of material to be injected.

FIG. 4 shows the device 10 at the rest or starting position, in non-exploded cross-sectional view, corresponding to the exploded cross sectional view of FIG. 3. In FIG. 4, the device 10 includes the guard 12 and the handle 18, the needle 24 and the chamber 20. Within the handle is the delivery mechanism 40 which includes a distal drive 42 and a proximal drive 44 that independently move within the handle 18. The distal and proximal drives are preferably electrically driven. Suitable drives are a stepper motor from Haydon Kerk (Waterbury, CT).

Also part of the delivery mechanism 40 is a threaded rod 46 which extends from the proximal end of the handle 18p, through the proximal drive 44, then through the distal drive 42, and terminates at its distal end 46d when in contact with the plunger 48 that fits within the chamber 20. In FIG. 4, the needle is in the retracted position, i.e., wholly within the guard 12, the distal and proximal drives 42 and 44 are adjacent to one another, and the proximal end 46p of the threaded rod 46 essentially fills the channel 50 which is located within the handle 18 and is of a size and dimension to receive the threaded rod 46. In FIG. 4, the device 10 contains a liquid (not shown) in the chamber 20 but is not yet ready to inject the liquid into a subject.

Figure 5:
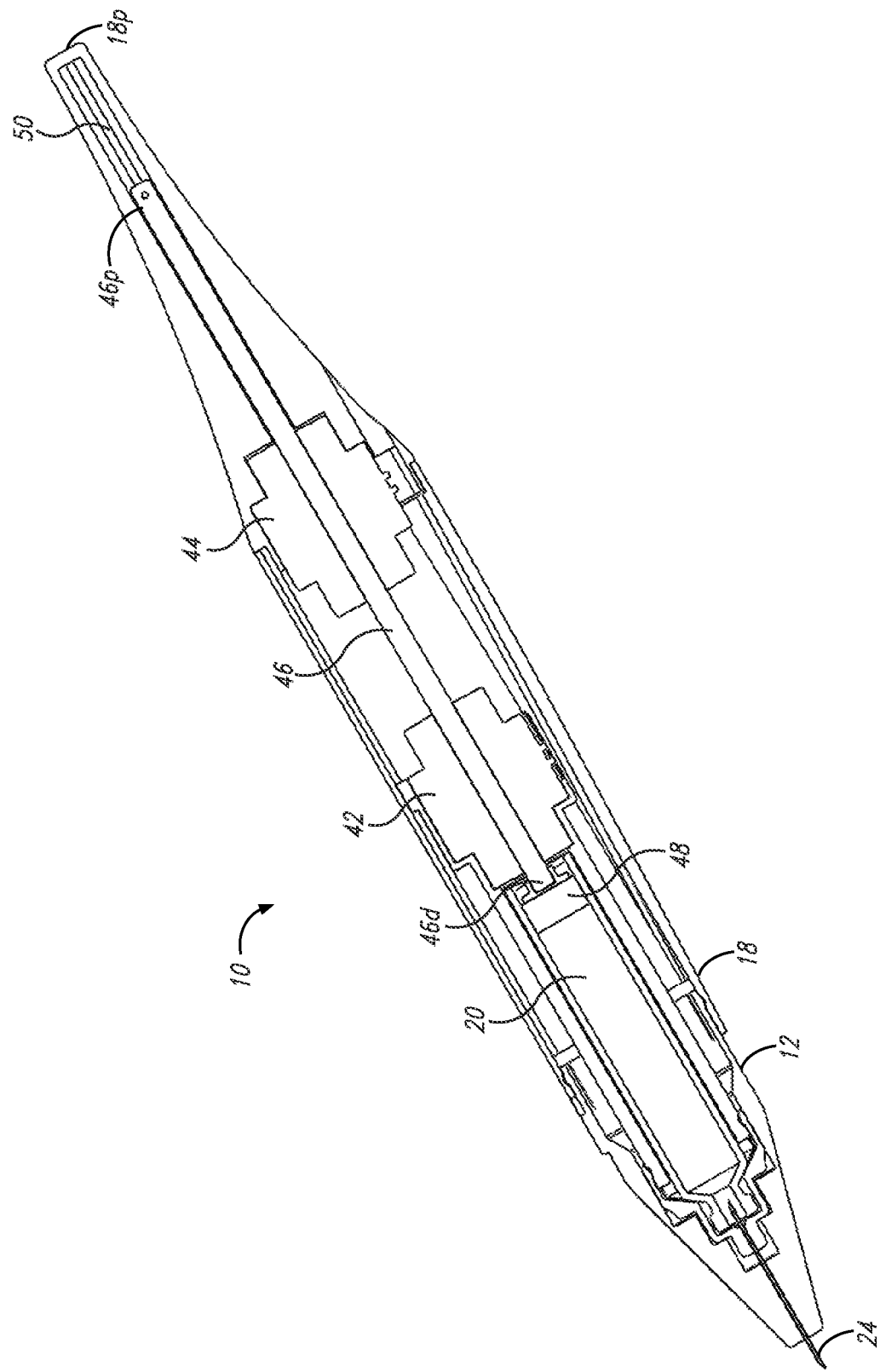
FIG. 5 shows a cross-sectional view of a preferred embodiment of the injection device, where the needle is in the extended position and the chamber is full of material to be injected.

FIG. 5 shows the device 10 at the injection position, in non-exploded cross-sectional view, corresponding to exploded perspective view of FIG. 3. In FIG. 5, the device 10 includes the guard 12 and the handle 18, the needle 24 and the chamber 20. Within the handle 18 is the delivery mechanism 40 which includes a distal drive 42 and a proximal drive 44 that independently move within the handle 18. Also part of the delivery mechanism 40 is a threaded rod 46 which extends from the proximal end of the handle 18p, through the proximal drive 44, then through the distal drive 42, and terminates at its distal end 46d when in contact with the plunger 48 that fits within the chamber 20. In FIG. 5, the needle 24 is in the exposed position, i.e., it extends outside the distal end 12d of the guard 12, and the distal and proximal drives 42 and 44 are not adjacent to one another but rather are spaced apart and separated by a distance of the threaded rod 46. Also, the proximal end 46p of the threaded rod 46 no longer essentially fills the channel 50 which is located within the handle 18 and is of a size and dimension to receive the threaded rod 46. Rather, the threaded rod 46 has moved a distance toward the distal direction 10d of the device 10, thus exiting a length of the channel 50. Thus, in FIG. 5 it can be seen that the proximal end 46p of the rod 46 has moved away from the proximal end 18p of the handle 18, thereby exposing more of the channel 50. In FIG. 5, the device 10 contains a liquid (not shown) in the chamber 20 and the exposed portion of the needle 24 is ready to be inserted into the skin of the subject. The chamber 20 has not changed in dimension between the starting position illustrated in FIG. 4 and the injection position illustrated in FIG. 5.

Figure 6:
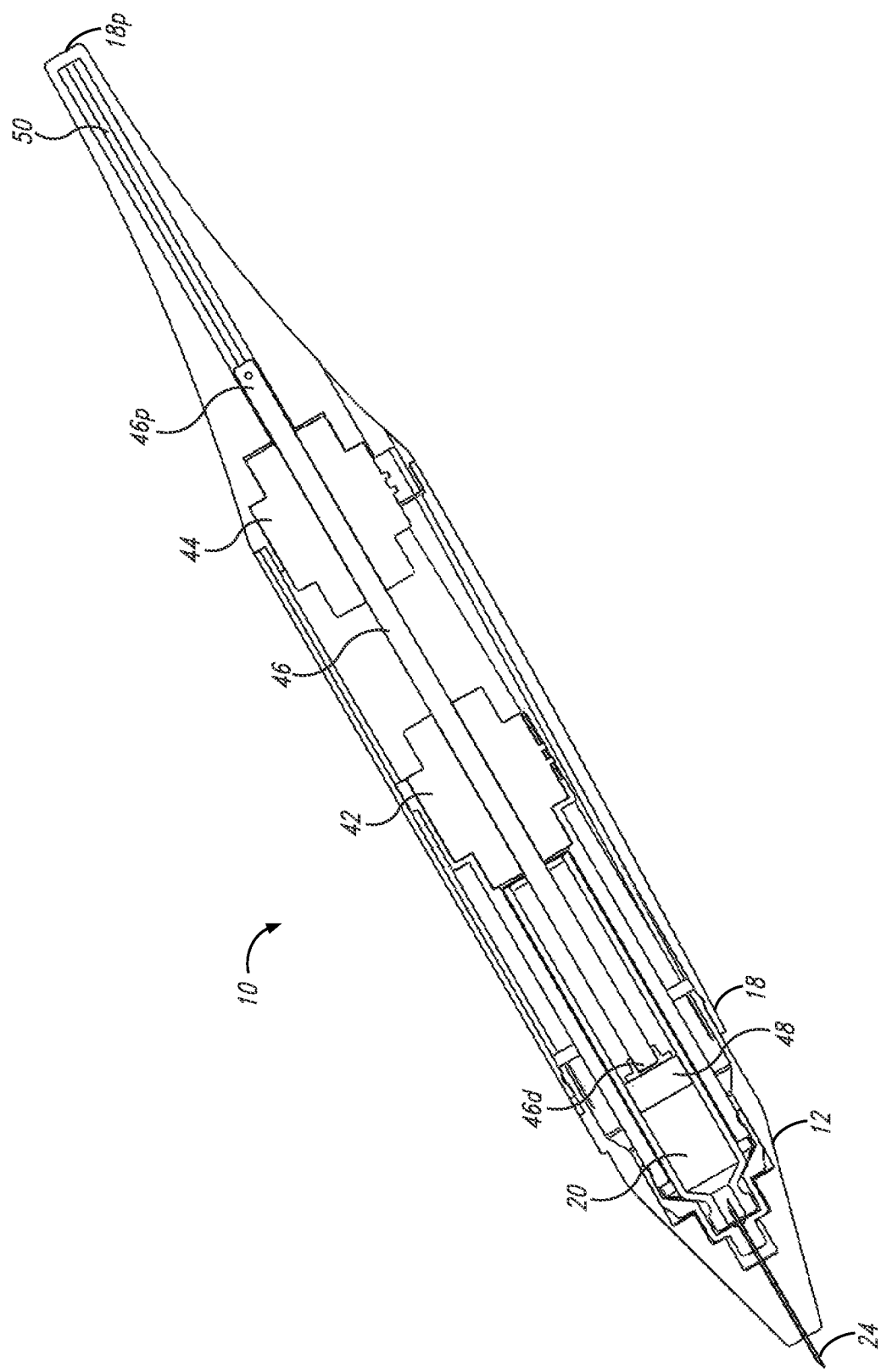
FIG. 6 shows a cross-sectional view of a preferred embodiment of the injection device, where the needle is in the extended position and the chamber is empty of material to be injected.

FIG. 6 shows the device 10 at the deposition position, in non-exploded cross-sectional view, corresponding to exploded perspective view of FIG. 3. In FIG. 6, the device 10 includes the guard 12 and the handle 18, the needle 24 and the chamber 20. Within the handle is the delivery mechanism 40 which includes a distal drive 42 and a proximal drive 44 that independently move within the handle 18. Also part of the delivery mechanism 40 is a threaded rod 46 which extends from the proximal end of the handle 18p, through the proximal drive 44, then through the distal drive 42, and terminates at its distal end 46d when in contact with the plunger 48 that fits within the chamber 20. In FIG. 6, the needle is in the exposed position, i.e., it extends outside the distal end 12d of the guard 12, in essentially the same position that it adopts in the injection position illustrated in FIG. 5. In FIG. 6, the distal and proximal drives 42 and 44 are not adjacent to one another but rather are spaced apart and separated by a distance of the threaded rod 46, in essentially the same positions that they adopted in the injection position illustrated in FIG. 5. In FIG. 6, and in comparison to the configuration shown in FIG. 5, the proximal end 46p of the threaded rod 46 has moved even further away from the proximal end 18p of the handle 18, so that even more of the channel 50 is empty. This movement of the threaded rod 46 in the distal direction 10d of the device 10 has caused the plunger 48 to move in the distal direction 10d, and thereby reduce the volume of the chamber 20. This reduction in volume of chamber 20 causes an increase in pressure within the chamber, which pushes the liquid contents of the chamber through the needle 24 and into the subject receiving the injection. This is referred to as the deposition position of the device 10.

In comparing FIGS. 4, 5 and 6, it can be seen that the delivery mechanism 40 works by the movement of the proximal and distal drives 44 and 42, respectively, which in turn causes the threaded rod 46 to move and hence the plunger 48 to extend into the chamber 20 and push the contents of the chamber out through the needle 24. In FIG. 4, the proximal and distal drives are in the rearmost, i.e., proximal-most, position. Likewise, the threaded rod is in the rearmost position. In order to extend the needle outside of the guard, the proximal drive is activated. This activation of the proximal drive causes the threaded rod, the distal drive, the chamber and the needle to all move in concert in the distal direction, thereby extending the needle outside the guard. The proximal drive, however, does not move in relation to the handle 18. This configuration is illustrated in FIG. 5. In order to eject the contents of the chamber through the needle, both of the proximal and distal drives are activated. This double activation causes only the threaded rod to move in the distal direction, where this movement pushes the rod against the plunger 48, thus decreasing the size of the chamber 20. Neither of the proximal or distal drives move during this stage of operation: only the rod and the plunger move, and the liquid contents are expelled from the chamber.

Figure 7:
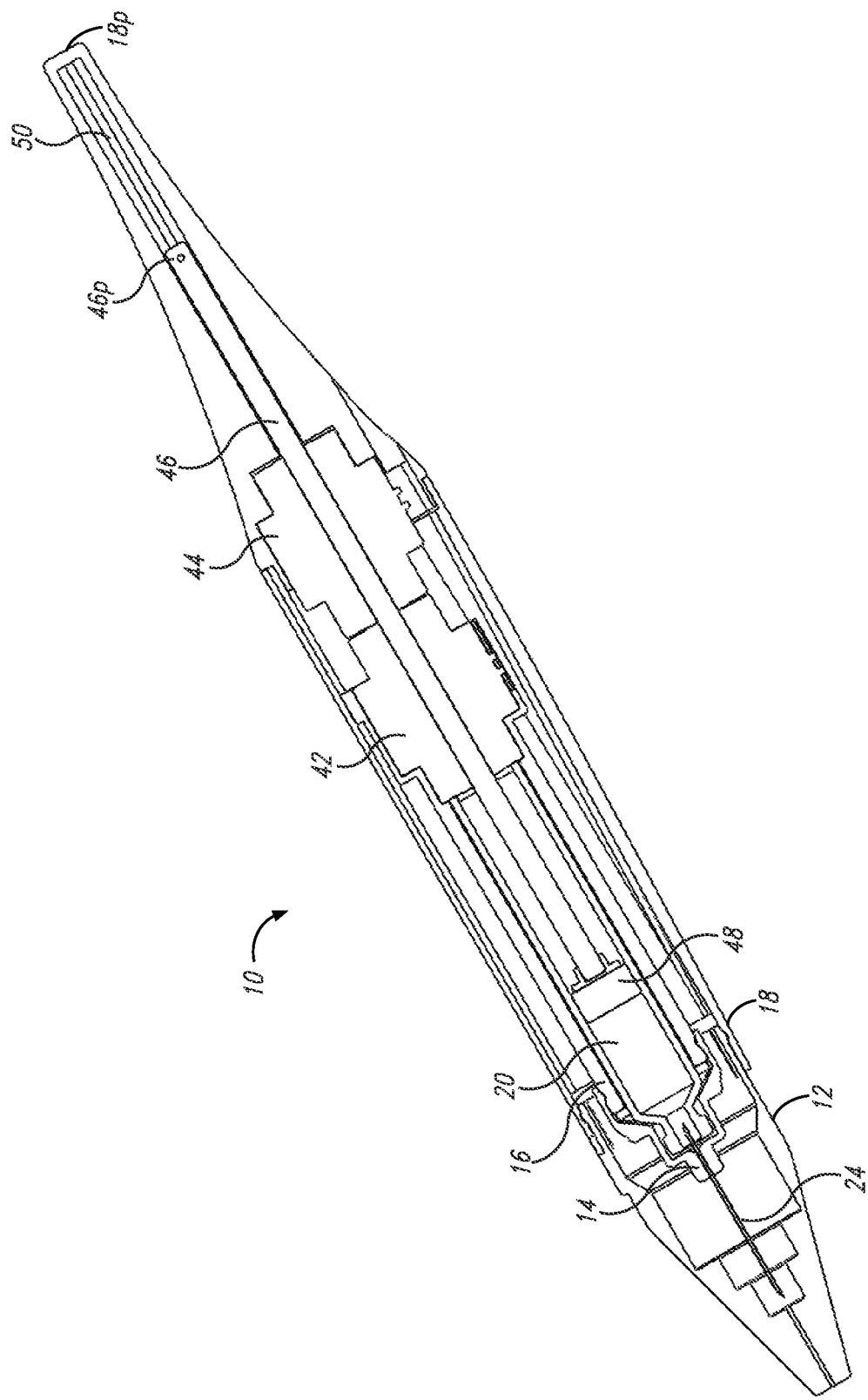
FIG. 7 shows a cross-sectional view of a preferred embodiment of the injection device, where the needle is in the retracted position and the chamber is empty of material to be injected.

After the contents of the chamber 20 have been injected into the subject, the needle may be retracted to a safe position. This is shown in FIG. 7. In comparison to the configuration of FIG. 6, the distal drive 42 has moved back into position adjacent to the proximal drive 44, i.e., those two drives are in the same position as they were in the resting position of FIG. 5. However, in comparison to FIG. 6, the plunger 48 has not changed location and the chamber 20 is of the same size as shown in FIG. 6. However, along with the movement of the distal drive 42, the threaded rod has moved in the proximal direction. This movement of the threaded rod in the proximal direction has effective pulled the injector 14 in the proximal direction, which has caused the needle 24 to move in the proximal direction and thereby withdraw into the guard 12. This movement of the needle from the exposed position of FIG. 6 to the shielded position of FIG. 7 is accomplished by activating the proximal drive 44 which causes the entire package consisting of the distal drive 42, the cartridge 16 and the injector 14 to move in the proximal direction.

In a preferred embodiment, the guard 12, the injector 14 and the cartridge 16 are disposable, while the handle 18 with the delivery mechanism 40 are re-usable.

Figure 8:
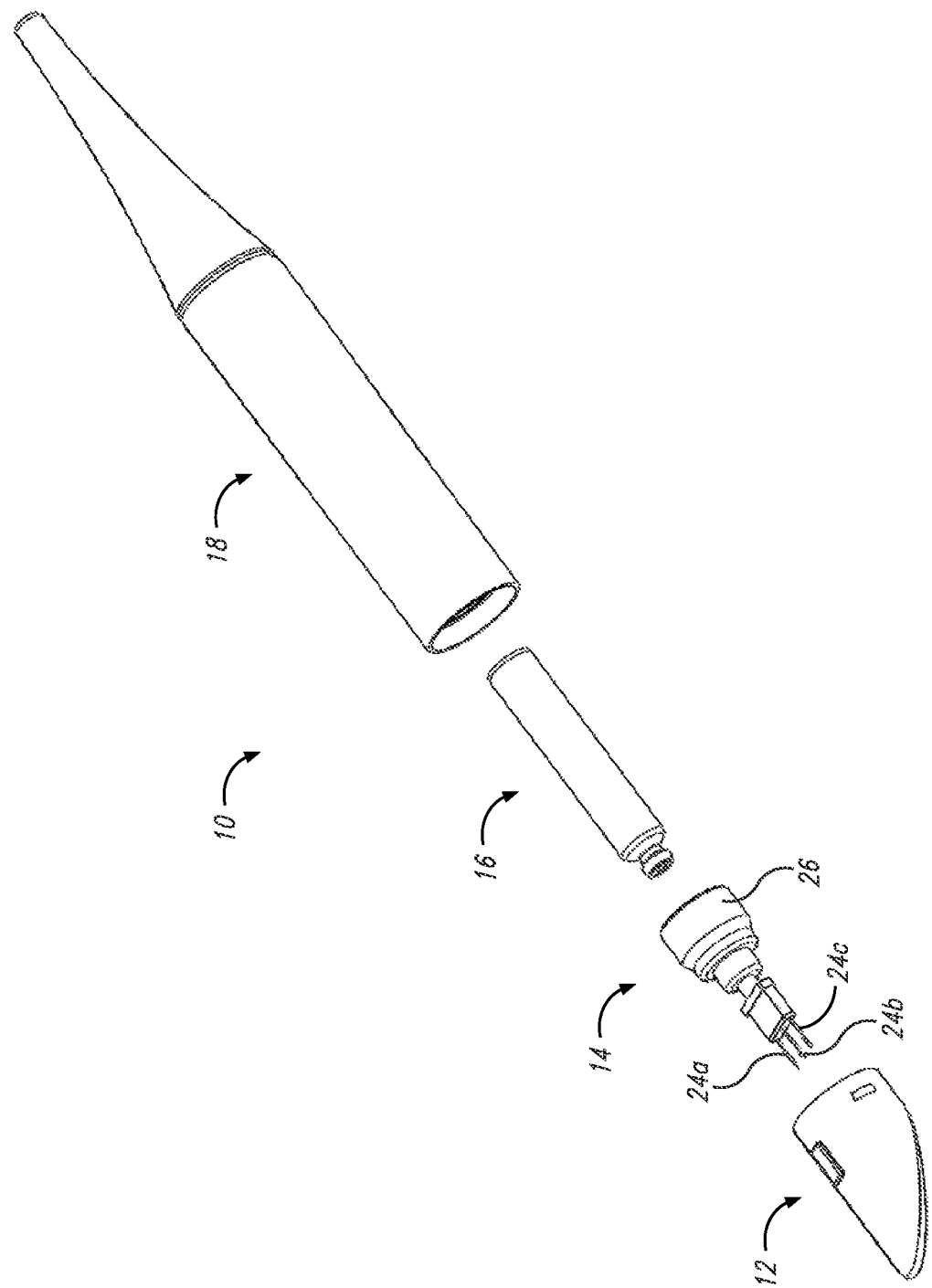
FIG. 8 shows a perspective view of a preferred embodiment of the injection device, wherein the device is shown in an exploded view to illustrate various parts of the device, including an optional guard and an injector with three needles.

FIG. 8 shows another embodiment of the injection device 10 of the present invention in an exploded perspective view. In this embodiment, the injector 14 contains three needles, 24a, 24b and 24c, all attached to a single housing 26. The cartridge 16 and the handle 18 are unchanged from the embodiment shown in FIG. 1. However, the guard 12 has a different shape, taking on the appearance of a shield that only partially encloses the needles even when they are in a retracted configuration.

Figure 9:
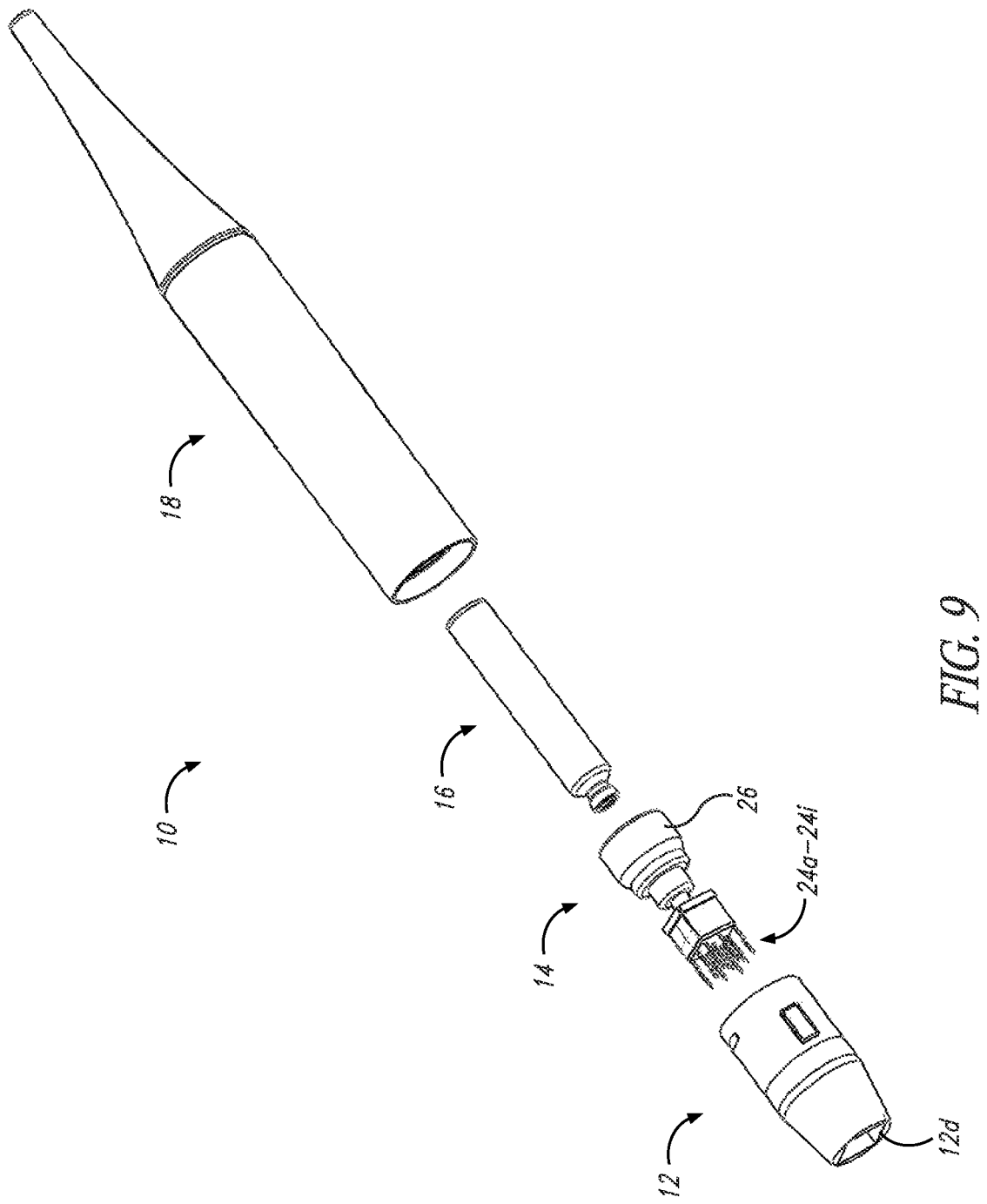
FIG. 9 shows a perspective view of a preferred embodiment of the injection device, wherein the device is shown in an exploded view to illustrate various parts of the device, including an optional guard and an injector with nine needles.

FIG. 9 shows another embodiment of the injection device 10 of the present invention in an exploded perspective view.

In this embodiment, the injector 14 contains nine needles, 24a, 24b, 24c, 24d, 24e, 24f, 24g, 24h and 24i, all attached to a single injector housing 26. The cartridge 16 and the handle 18 are unchanged from the embodiment shown in FIG. 1. However, the guard 12 has a much larger opening at its distal end 12d in order to accommodate the greater size of the array of needles attached to the housing 26.

Figure 10:
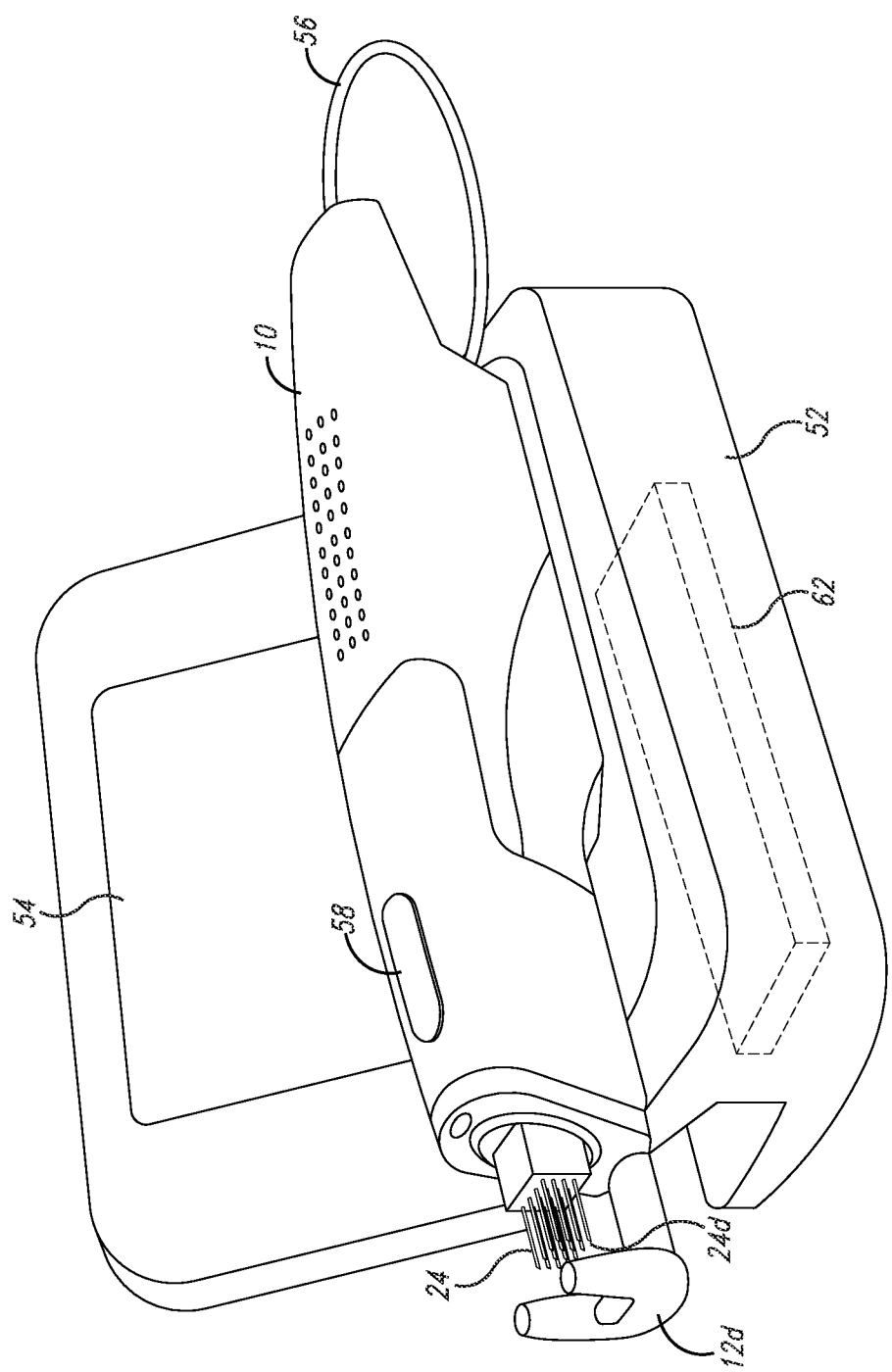
FIG. 10 shows a perspective view of an embodiment of a dermal injector of the present disclosure having an injection device and a docking station with a touch screen.

FIGS. 10-13 show perspective views of an embodiment of a dermal injector of the present disclosure. In FIG. 10, the injection device 10 is sitting in a docking station 52, where the docking station 52 includes a touch screen 54 which can receive and display information. As described in the present disclosure, the docking station 52 may optionally include a control unit 62 (FIG. 14) integrated therein or otherwise coupled thereto. A cable 56 connects the injection device 10 and the docking station 52 in the embodiment of FIG. 10, though it is recognized that in some embodiments, the injection device 10 may be wirelessly coupled to the docking station 52. The injection device 10 is joined to the guard 12 as shown by the distal end of the guard 12d. The injection device also includes an activator button 58 which, when depressed, activates the injecting mechanism so that the needles advance past the end of the guard 12d and into the tissue that is adjacent to the surface 12d.

Figure 11:
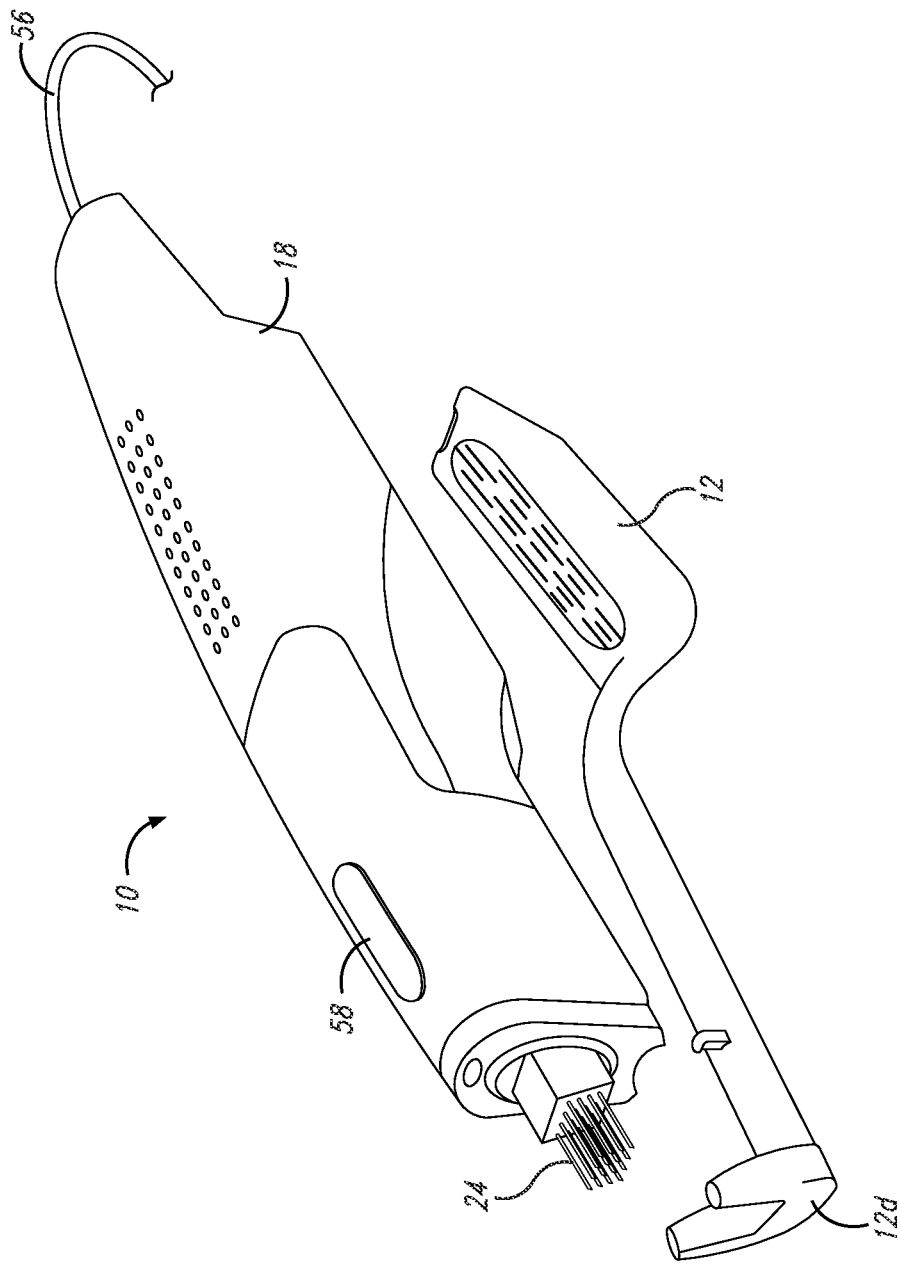
FIG. 11 shows a perspective view of an embodiment of an injection device of the present disclosure, including an optionally removable cooling unit.

In FIG. 11, an embodiment of an injection device 10 of the present disclosure is shown. The injection device 10 includes an array of needles 24 (e.g., 4×4, which is illustrative of the arrays that may be incorporated into the injection device) and a guard 12 which fits onto the handle 18 of the injection device and both sets limits on the distance between the needles 24 and the tissue to be injected, and incorporates a cooling element at its distal end 12d. In order to adhere exactly to the needle insertion depth, the distance from the needle tip or tips 24d to the area that will be placed on the skin must be precisely defined, and this is achieved by way of the attached guard 12. In operation, the syringe carriage approaches a reference position, so that the distance from the needle tip 24d to the area that will be placed on the skin is precisely defined. The injector device assumes this reference position based on the position of the carriages which the needle and the syringe are positioned on, being referenced relative to the cooling component attachment/guide 12. This reference position is detectable with a suitable sensor. The reference position can also be the position which the needle assumes between two applications. This guard attachment 12 also sets the angle through which the needles 24 will travel on their way to entering the tissue. Optionally, this angle may be adjusted by a screw or other mechanism (not shown) that adjusts the angle between the bottom of the attachment and the longitudinal axis of the needle array.

Figure 12:
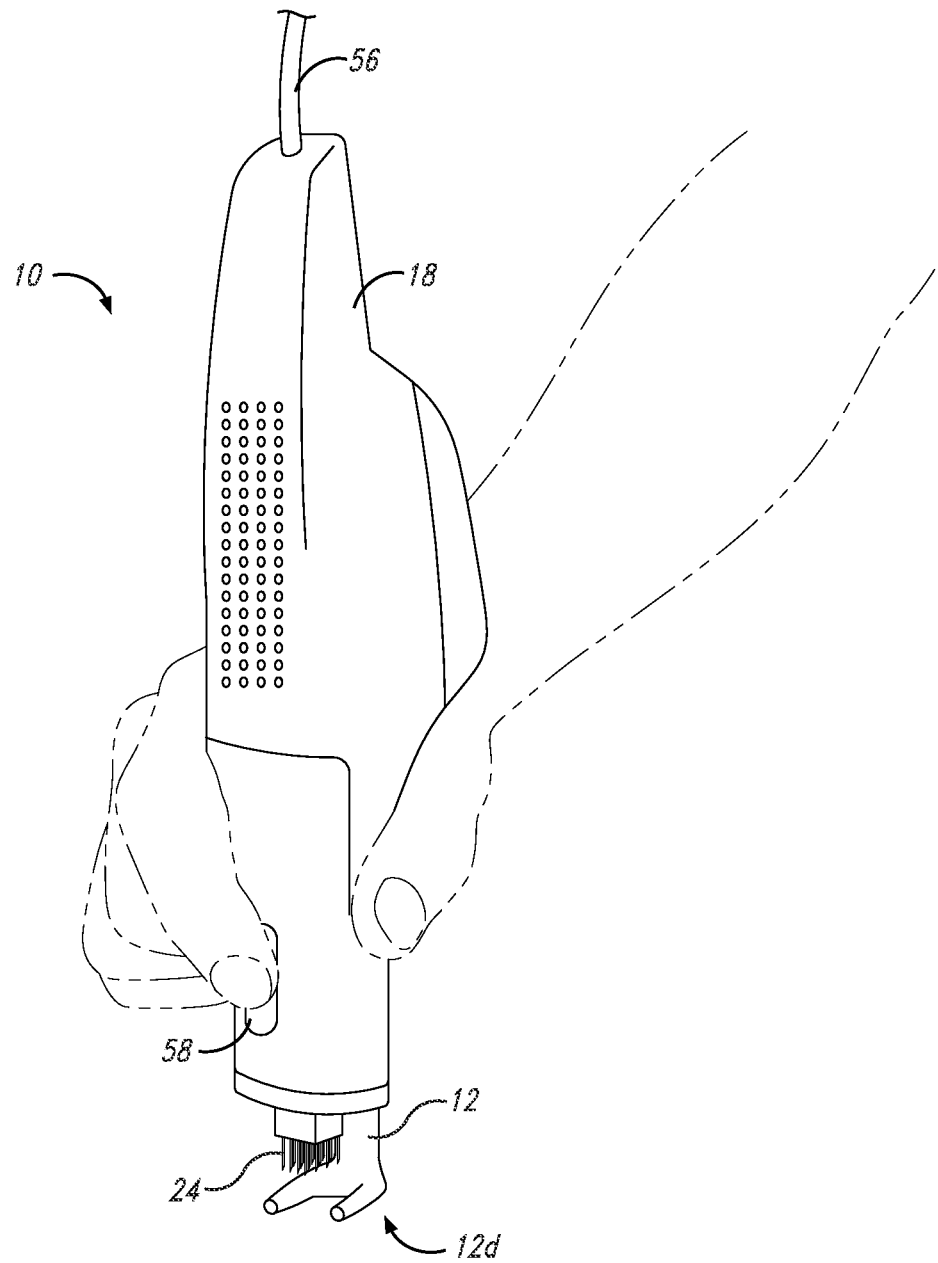
FIG. 12 shows a perspective view of an embodiment of an injection device of the present disclosure, being held by a clinician in a state ready to initiate an injection.

In FIG. 12, an embodiment of an injection device of the present disclosure is shown in the hands of a clinician who is ready to trigger an injection into a subject by pushing on a button 58 located near the needles 24. In FIG. 12, the angle of the needle array is perpendicular, i.e., at 90 degrees, to the surface of the skin, where this angle is set by the geometry of the cooling unit guard attachment 12, and in particular the surface at the distal end 12d of the guard 12. Optionally, the cooling unit guard attachment 12 may be selected from a plurality of cooling unit attachments which differ from one another by the angle between the longitudinal axis of a needle in the needle array and the plane of the surface of the cooling unit that is pressed against the tissue adjacent where the injection will take place. In one embodiment, that angle is 90 degrees and the corresponding injection may be referred to as a vertical injection.

Figure 14:
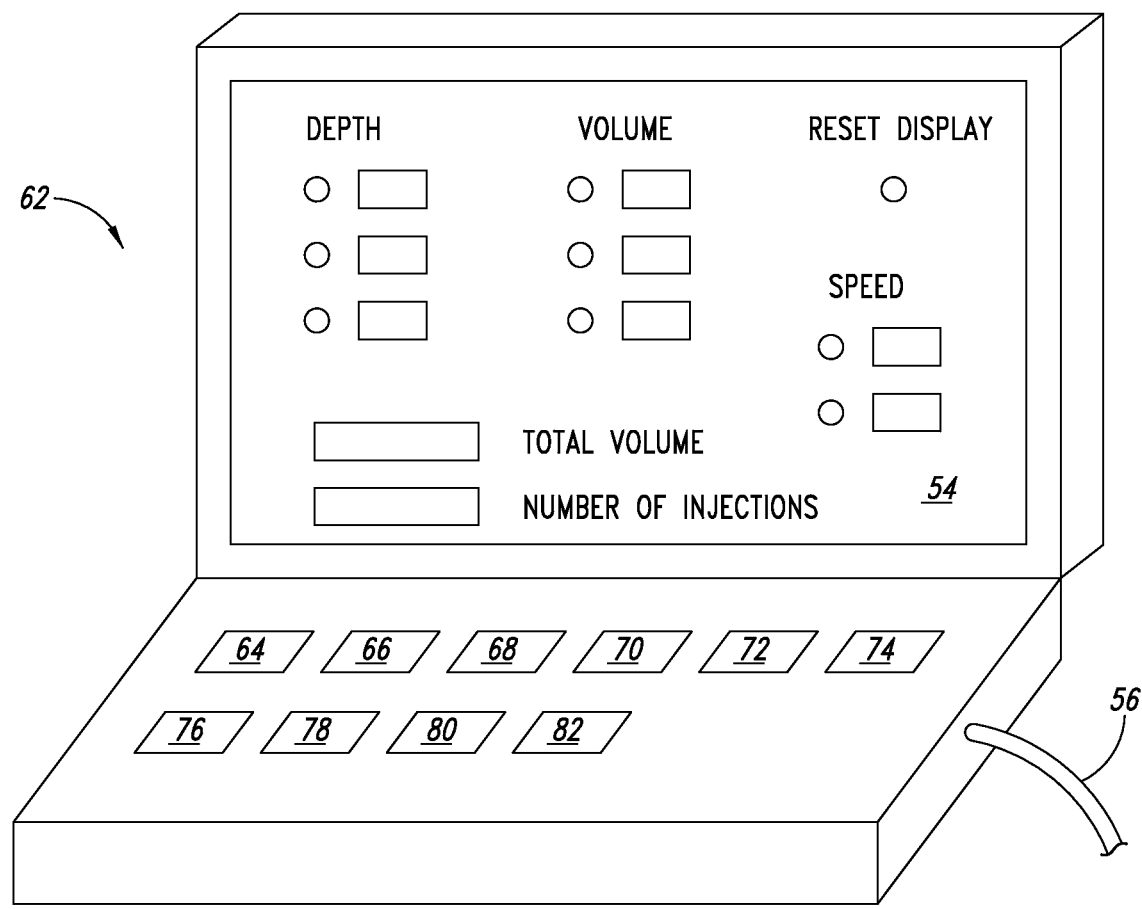
FIG. 14 shows an exemplary display of the control unit.

Optionally, the handle 18 with the attachment guard 12 cannot fit into the docking station 52. This embodiment discourages re-use of the cooling unit (that forms part of the guard 12) between injections, particularly injections with different patients. In this embodiment, the cooling unit guard attachment 12 must be removed from the hand-piece 18 in order for the hand-piece 18 to be stored in the docking station 52 until the dermal injector is ready to be used again. During this intermediate time, the cooling unit guard attachment 12 may be stored in a sterile packaging away from the control unit 62 (FIG. 14).

Figure 13:
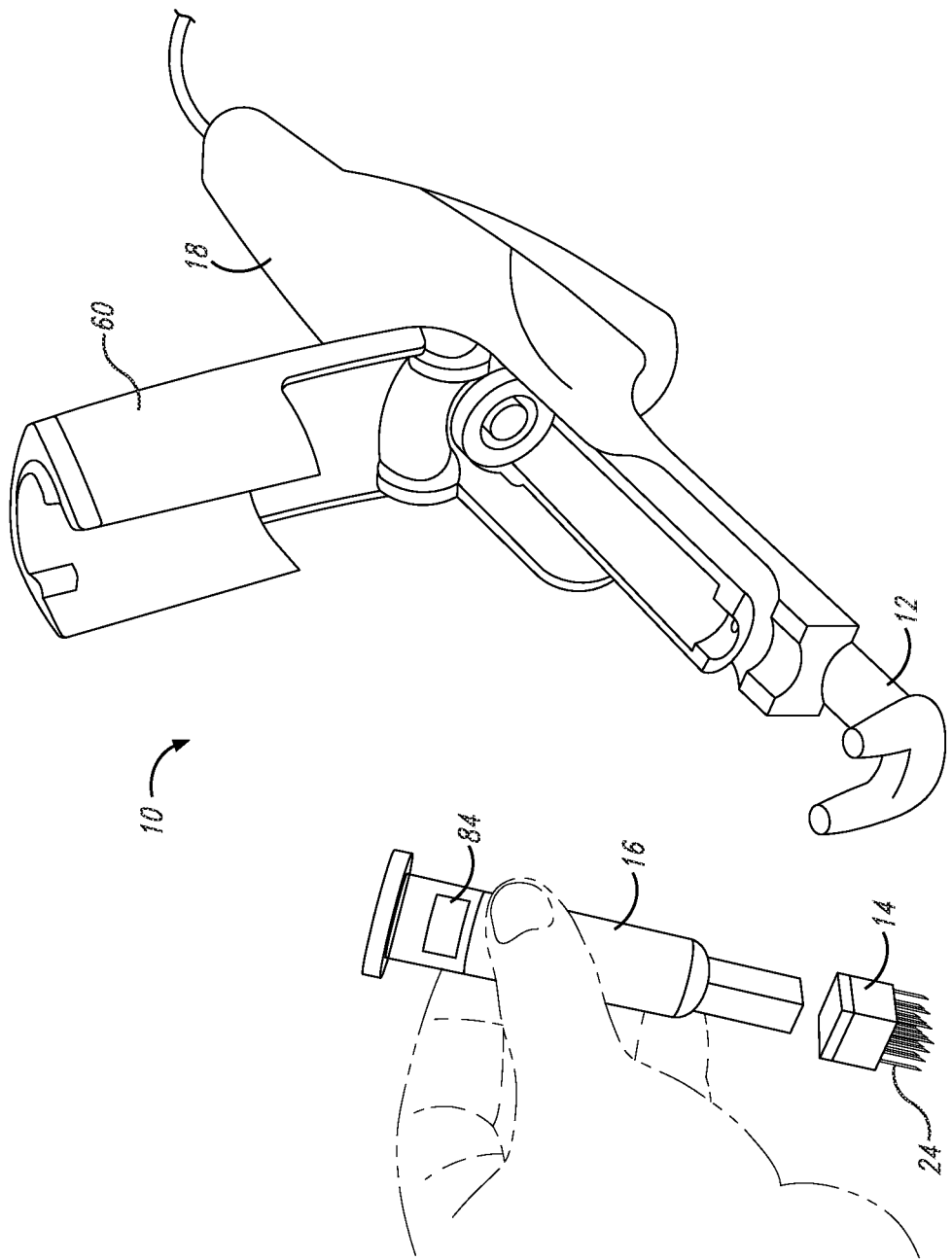
FIG. 13 shows a perspective view of an embodiment of an injection device of the present disclosure, having an open flap ready to receive a pre-loaded cartridge (also shown) of material to be injected.

In FIG. 13, an embodiment of an injection device 10 of the present disclosure is shown in an open form, i.e., the top or flap 60 of the handle 18 has been rotated open on a hinge to reveal a central cavity where the syringe cartridge 16 may be placed. The cartridge 16 may be pre-loaded with the material to be injected into the subject. The cartridge 16 may comprise a source of information about the cartridge and the contents of the syringe, e.g., the material in the syringe may be identified by data on an RFID or barcode 84 attached to the cartridge or syringe. In some cases, the RFID, barcode, or other communication device 84 is electronically accessible by the control unit 62 or another device. The communication device 84 may be a form of Digital Rights Management, e.g., an identifiable tag or marker. Examples include RFID tags (and alternatives such as HP Memory Spot and RuBee (IEEE 1902.1)), ink markings, QR codes and barcodes. The Digital Rights Management (e.g., identifiable tag or marker) can be arranged to store information about material in the cartridge, where such information may also include, for example, the composition to be delivered, manufacturer, date of manufacture, lot number and/or serial number.

The control unit 62 or other device is arranged to interrogate the syringe cartridge 16. In some cases, the RFID, barcode, or other communication device 84 delivers static information, such as regulatory information regarding the source of the material in the cartridge, dosage, lot number, or another uniquely identifiable identifier. In other cases, particularly where an RFID or other communication device 84 is included with the syringe cartridge 16, information regarding the syringe cartridge 16 is dynamically arranged. In this way, first use of the cartridge, most recent use of the cartridge, number of doses, coupling of a particular dosage to a particular patient, and other information may be recorded or stored on the syringe cartridge and later retrieved by the control unit 62 or another device.

The dermal injector of the present disclosure is preferably electrically operated. Thus, a control unit 62 is linked to the hand-piece via a wired connection such as a cable or via a wireless connection. The cable is preferably flexible, without memory and preferred direction, and without strong twist (so that little resistance is encountered if the cable is twisted). The cable may have a diameter of about 6 mm and a length of about 3 meters. The cable may have a plus symbol on the reverse of the control unit 62. The cable between the control unit 62 and the handheld unit preferably provides both data connection and power supply. The control unit 62 may be located within the docking station 52. The control unit 62 has an on/off switch. The on/off switch allows that the whole system may be switched on or off via a switch, e.g., a rocker switch.

The control unit 62 receives information about the desired penetration depth of the needle, also referred to as injection depth. The control unit 62 also receives information about the desired delivery volume. This information may be provided by the cartridge itself that contains the material to be delivered. Thus, an information reading and tracking feature may be incorporated into the device of the present disclosure. That tracking feature may take the form of a bar code, or an RFID (radio frequency identification) chip, or some other communication device, any of which may be associated with the material to be delivered and optionally with the patient that is receiving the material. The controller system of the dermal injector device of the present disclosure will recognize the information contained in the RFID and automatically adjust operation controls as appropriate, i.e., the device will set the needle depth, speed of injection and amount of injection which is appropriate for the procedure. For example, different injection controls are suitable for different fluids and substances, and these injection controls may be established automatically once the controller system recognizes the information on the RFID or other detection system. The controller system may also be programmed to provide a computerized record of a treatment. For example, the record may indicate one or more of the subject's name, the treatment provider's name, the institution or office providing the treatment, what was injected, how many times it was injected, the amount that was delivered, the depth of injection and when that delivery took place. The software of the controller system may be programmed to ensure that the needles do not go too deeply into tissue. The software may also check to see that the material identified as being present in the cartridge is an approved material for delivery to this patient.

Alternatively, or additionally, parameters such as injection depth may be manually input into the controller system. These may be pre-defined, e.g., there may a fixed number of options, e.g., three options to select from so to provide three different fixed injection depths. A capacitive button may be present on the control unit 62 which will respond to input from the user. A transparent glass or plastic pane or cover may be placed over the capacitive button(s) and display(s), where relevant printing is placed on the back of the pane and clearly visible to the user (but protected from frictional forces which will rub away the writing or other images). When the user presses against the surface of the panel, at a location above a capacitive button, the control unit 62 will thereby receive input from the user which selects a penetration depth of needle. Optionally, the capacitive button may be placed underneath the word "depth" where three lights are adjacent to this word, each light corresponding to a different injection depth. When the user touches the location above the word "depth", a light will illuminate the shortest injection depth value. A second touch of the word "depth" will cause the light to move to the medium injection depth value, i.e., the shortest injection depth value will no longer be illuminated. A third touch of the "depth" location on the panel simultaneously causes the illumination of the medium injection depth value to cease, and an illumination of the longest injection depth value to occur. In this way, the user may toggle through three different pre-set injection depths, and know which injection depth has been selected because the selected injection depth, and only the selected injection depth, is illuminated. Of course, the number of options may be more or less than three.

The delivery volume, also referred to as application volume or injection volume, may also be selected via user interaction with the control unit 62, e.g., with a touch screen of the control unit 62. These delivery volumes may be pre-defined, e.g., there may be three options to select from so as to provide three different injection volumes. The control unit 62 may have a visual indicator of the overall injection volume that has been selected. In addition, the display may show the total volume being injected. The control unit 62 can calculate this value based on the selected injection depth, selected injection volume and the number of injections. The number of injections is determined by the head of the injector, and the control unit 62 may be programmed to recognize unique delivery heads and the number and size of needles present on a particular delivery head. The control unit 62 may have a visual indicator of the number of injections that have been selected.

FIG. 14 provides one exemplary illustration of how the display feature of the control unit 62 may look. FIG. 14 also illustrates functional logic modules (i.e., components) of the control unit 62. One or more processing units 64 are coupled to one or more internal and/or external memories 66 via a bus (not shown). A bus as used in the control unit 62 includes one or more wired or wireless data paths that communicatively couple some or all of the internal and/or external components of the control unit 62. The various components shown in FIG. 14 may be part of an independent control unit 62, part of a docking station 52, or in some cases, some or all of the components may even be integrated in the injection device 10.

Input/output (I/O) ports 68 permit the control unit 62 to output data and receive data from external sources such the injection device 10, the Internet, a clinician, or an external computing device. In some cases, the I/O ports 68 are cooperatively coupled to components of the control unit 62 such as touchscreen 54 and other components not shown in FIG. 14. For example, in some cases, the I/O ports 68 are coupled to keypads, secondary displays, feedback devices, alarms, aiming controllers, motion devices, computing devices, distance measuring devices, or other components operative within the dermal injector. In some cases, the I/O ports 68 facilitate the input of new software programs, initialization parameters, control data, and the like.

The I/O ports 68 of FIG. 14 include general purpose I/O ports that are configured for determined operation with devices of the control unit 62. The I/O ports 68 also include communication ports that may follow one or more standardized or custom protocols such as RS-232 or RS-485 serial communications, universal serial bus (USB), parallel port, IEEE-1394 communication, and the like.

In some embodiments, the I/O ports 68 facilitate the output of recorded data or other parameters of the dermal injector. For example, the control unit 62 may capture image data, drug control dosage information, patient information, or other like information in memory 66 for some period of time verification, post-injection analysis, regulatory requirements, or other purposes. Additional image data may also be captured before, during, or after an injection. The data capture time period may be 10 seconds, 5 minutes, or some other time period. In some cases, the image data may be captured at a higher resolution than when other data is not being captured, and in other cases, the resolution may be lower. Additional data related to the dermal injector such as environmental parameters, user parameters, and the like may also be captured.

After the stored data is exported from the dermal injector via I/O ports 68, the data may be analyzed. A full re-creation or post-event study of an injection event can subsequently be created. For example, in one embodiment, a video showing events before, during, and after an injection may include high or low resolution images, moving images, and audio. Additional data related to the video may include settings and recorded values related to environmental sensors, accelerometers, and the like may also be captured. The additional data may be synchronized in time with the video.

The control unit 62 may include audio devices 70. The audio devices 70 may be speakers or other devices capable of reproducing a wide range of frequencies in the audio spectrum. For example, if the control unit 62 includes a feature for voice commands to direct a clinician during an injection, the audio device 70 may project the voice commands.

In other embodiments, the audio devices 70 are piezo or like devices that project tones of one or more frequencies to alert the clinician to determined events. The tones may be single beeps, interval beeps, or solid tones. In one embodiment, a beeping series of tones are sounded as an injection is administered. The beeps may rise in volume and/or frequency to indicate increasing confidence as the device approaches a determined threshold level. When the confidence threshold is met, the beep may change to a solid tone. In other cases, the tones are used in other ways and for other purposes, for example, to denote or reflect depth of an injection, volume of material injected, low battery or fully charged battery indicators, keypress acknowledgment, and the like.

Many embodiments of the control unit 62 include a display controller 72 coupled to a display in the touchscreen 54 or some other visual output device (not shown). The display controller 72 may provide mono-color, gray-scale (e.g., black and white), or multi-color display output. The display controller 72 in FIG. 14 has an integrated touchscreen controller, but a separate touchscreen controller is also contemplated. In some cases, selected display icons are also controlled by the display controller 72. For example, display icons may include a battery indicator, a depth indicator, volume of delivered material indicator, a reset indicator, a total volume indicator, a number of injections indicator, and other indicators. The indicators may be formed as a circle, a square, a rectangular box icon, or some other shape. In some cases, a day or night ambient light sensor indicator (not shown) controls backlight or other brightness of the display. The display used in cooperation with touchscreen 54 may be a liquid crystal display (LCD), light emitting diode (LED), or some other technology. The display may have a portrait, landscape, square, or another orientation. The display may have quarter video graphics array (QVGA), half VGA, full VGA, resolution or some other high resolution or low resolution configuration. In some cases, the display may be a substantially transparent display only having particular icons affixed over the optical viewing area of permanently affixed icons.

Embodiments of the control unit 62 of FIG. 14 include one or more camera devices 74, for example, the computer-vision technology described herein. The camera 74 is typically aimed in a target direction of the patient and configurable to provide image data to the control unit 62.

The cameras 74 may include charge couple devices (CCD), complimentary metal-oxide semiconductor devices (CMOS), or some other image sensor technology. The imaging sensors may be arranged as an array of pixels or in some other configuration. The imaging sensors are configurable to provide a single image data frame or a plurality of data frames (e.g., a series of sequential images). The number of pixels in a camera 74 array may determine that the camera 74 is configured as a high resolution camera, a low resolution camera, or some other resolution.

The dermal injector may include one or more environment sensors 76 configured to produce environment data samples. The environment sensors 76 are illustrated in the control unit 62, however it is recognized that environment sensors may be placed in other areas of the dermal injector, such as the injection device 10, the docking station 52, or elsewhere. The environment sensors 76 may sense temperature, humidity, altitude, air density, air pressure, ambient light, motion, or other environmental conditions. The sensors 76 provide analog or digital environmental data to the control unit 62. The environmental data may be cooperatively used with other data by the processor 64 to calculate ambient background light, temperature of the cooling tip, and many other parameters.

Embodiments of the dermal injector may include one or more system outputs passed through the I/O ports 68. System outputs include outputs to control or prevent the actuation of delivery mechanism 40. For example, in some embodiments, the processor 64 can direct the step motor or a controller for the step motor (e.g., solenoids, actuators, etc.) to advance or retract the distal drive 42. In other embodiments, micro electro-mechanical system (MEMS) devices such as a gyroscopic device or a pressure device prevent actuation if a needle has not been changed between injections. System outputs also may include devices to assist the image data producing cameras 74 such as light beam producing devices (e.g., for improved vision and imaging), thermal imaging, autofocus, and other devices.

In some embodiments, the dermal injector includes one or more user input devices that pass data through the I/O ports 68. The user input devices may include sliding switches, push buttons, scroll wheels, rotating knobs, and the like connected to electronic input devices such as switches, potentiometers, capacitive input devices, and other components. The input devices may be operated by a clinician to provide particular determined parameters for use by the dermal injector. For example, a clinician can manipulate input devices (e.g., touchscreen 54) to provide depth, volume of material injected, total volume, number of injections, a safety lockout of the dermal injector, an operating mode, and many others. Additionally, the input devices may be used to provide data inputs to calibrate environment sensors 76, cameras 74, and other devices. Additionally still, the input devices may be used to power on/off the dermal injector, enable/disable the dermal injector, reset one or more values such as the total volume or number of injections of the dermal injector, change operating modes, change display views on the display, store, review, and/or delete data from memory, and perform many other functions.

One particular input illustrated in control unit 62 is an RFID controller or other communication device controller 78. The RFID controller or other communication device controller 78 is generally arranged to communicate with an RFID or other control device 84 on a cartridge 16. In some cases, the communication is bidirectional. That is, the control unit 62 and the cartridge 16 exchange information. In other cases, the communication is in one direction only. In these cases, the control unit typically reads data from the cartridge 16.

The dermal injector includes a power source 80. In some cases, the power source 80 includes a disposable or rechargeable battery as described herein. The power source 80 provides electrical power to the processor 64, memory 66, environmental sensors 76, and other components of the control unit 62. In some cases, charging and/or discharging of the power source is controlled by the processor 64.

In some embodiments, the control unit includes a coupling port 82. The coupling port 82 may permit the injection device 10 to affirmatively mate with the docking station 52 (FIG. 10). In these cases, an electrical or electromechanical coupling between the injection device 10 and the control unit 62 may be made. The coupling port 82 may include mechanical registration features to prevent or otherwise reduce the likelihood that the injection device 10 is misplaced into the docking station 52. In other cases, the coupling port 82 may be arranged such that particular pins of the coupling port automatically detect pins of the injection device 10 and perform an auto configuration operation. Through the coupling port 82, power may be passed to charge a battery in the injection device 10. In addition, or in the alternative, information may be communicated between the control unit 62 and the injection device 10.

Values for injection depth and injection volume are illuminated when that particular value is selected. A light may appear on the display if the control unit 62 parameters are being reset. The total volume being delivered and the total number of injections being delivered may also be displayed.

Light may be provided which will illuminate the injection point on the injection device. The light is preferably able to be switched on and off. A toggle switch may be used for this purpose. The control unit 62 may have a visual indicator of whether the light is on or off, e.g., the status may be displayed with background illumination.

The control unit 62 may also have a "clear" or reset button. This button is used to set all the values back to zero, in order to enter a new set of values. This may also be referred to as a dedicated reset button. Next to the button (or light) the control unit 62 may read "reset display" or similar meaning term. Reset may occur after the reset portion of the panel has been pressed for a pre-determined amount of time, e.g., 2 seconds or 2.5 seconds, in order to minimize the occurrence of an unintentional re-set.

In making calculations, the controller 62 may be provided with the following assumptions. Injection of material only occurs when the needle(s) are being withdrawn from the tissue. The speed during insertion and withdrawal of the needle remains at a constant value. However, the device may be capable of operating at two different speed levels: one speed (e.g., 10 mm/s max) if the syringe carrier is between the service position and the reference position, and a different speed if the syringe carriage is outside the above defined high speed range, which means while an injection sequence is in progress. These two speeds also apply for the piston rod: a lower maximum speed of e.g., 2 mm/s while an injection sequence is in progress, and a higher speed for the remaining activities like searching contact with the piston, retraction to the service position, etc. Other assumptions may also be provided to the control unit 62, also referred to as the controller.

The hand-piece, which may also be referred to as the injection device, has several components. For example, it may contain a motor assembly also referred to as the motor unit, which is reusable and is preferably amenable to wet disinfection. The motor unit contains one or more of the drive motors, the electronics, the fan, the syringe carriage and the holders for the cooling unit. In addition, the hand-piece contains a syringe, which is disposable and sterile. The hand-piece comprises a receptacle for the syringe which contains the filler or other material to be injected. In preparation for operation, the syringe is placed in the motor unit. The receptacle may be an enclosed space, accessed through a lid or flap that is removable and can be fitted back in place after the syringe has been removed or placed in the hand piece. As shown in FIG. 13, the lid may be attached to the hand-piece via a hinge which allows the lid to be opened and closed.

In addition, the hand-piece includes a needle assembly, which is preferably sterile and disposable. The needle assembly may contain an array of needles, and may be referred to as a pincushion design. In various embodiments, the needle array contains more than 2, 3, 4, 5, 6, 7, 8, 9, 10, 11, 12, 13, 14, 15, 16, 17, 18, 19, 20, 21, 22, 23, 24, or 25 needles. Within further embodiments the needles may have a gauge of 18, 19, 20, 21, 22, 23, 24, 25, 26, or 27. The array of needles is advantageous in that it allows for the injection of large volumes of material at a single time. In addition, the hand-piece may have a button or trigger which initiates the injection. This button is pressed after the hand-piece has been brought into the proper position. The injection sequence is activated via a push button that is located on the hand-piece, e.g., on the cover of the injector. The electric connection to the pushbutton can either be realized by cabling that is routed via the hinge or by contact pins. Another option is to have an electric push-button that is placed off-cover while a mechanical activation device is integrated into the cover and then transfers the compressive In addition, the hand-piece includes a comfortable handle and optionally, a connection to a data cord (power cord). The hand-piece is preferably light and well-balanced in order to make is easy to handle.

In addition, the hand-piece may have a cooling assembly, also referred to as the cooling unit. The cooling unit is preferably reusable, and accordingly should be amenable for sterilization, such as steam sterilization as provided by an autoclave. The cooling unit may comprise a Peltier element, which will be positioned on the skin to help numb the area to be treated. The cooling unit forms one single component and comprises the Peltier element, the head pipes and the cooling component. In order to permit steam sterilization, the cooling unit is removable from the hand piece. In one embodiment, the hand piece will not operate without the presence of the cooling unit. The cooling unit may be incorporated into the guard that partially shields the needles from contact. The cooling assembly may also comprise a plurality of thin copper sheets and the gaps between this sheeting can be air cooled by the use of a fan incorporated into the cooling assembly. The hand-piece will therefore emit some sound, i.e., the sound of a fan blowing.

The cooling unit will terminate in a surface, typically in the form of a plane, which will ultimately contact the skin of the subject receiving the injection. This surface may be U-shaped as shown in FIGS. 10-13. The U-shape geometry is advantageous in that it provides sufficient cooling to the tissue receiving the injection, but does not provide too much surface area to overburden the cooling unit's capacity. It is also important that the operator be able to see the puncture point of the needle(s). The U-shaped geometry provides this view without undesirable obstruction.

The cooling unit is preferably able to cool the region of the tissue receiving the injection to a temperature of less than 8 degree Celsius, optionally to a temperature of about 6 degrees Celsius, or about 4 degree Celsius. The tissue is preferably cooled to a temperature of greater than 1 degrees Celsius in order to avoid injury to the tissue.

In order to operate the dermal injector of the present disclosure, the operator preferably interacts with the control unit 62 in order to select one of three (or two, or four or more, but the operation will be illustrated with three) possible injection depths and one of three (or two, or four or more, but the operation will be illustrated with three) possible injection volumes. To emphasize, the present invention is not limited to three pre-set values. Injection depth may have 2 or 3 or 4 or 5 or 6 or up to 10 pre-set options, while likewise but independently, injection volume may have 2 or 3 or 4 or 5 or 6 or up to 10 pre-set options.

After injection depth and injection volume have been selected, a sterile cooling system is attached to the injector. The cooling system can be attached at any time, conveniently when the device is switched off. Presence detection by temperature signal is an optional feature of the device and its operation. The sterile cooling system may be incorporated into the guard 12.

The dermal injector may then be turned on. An on/off rocker switch may be used for this purpose, where the rocker switch may be located on the control unit 62, e.g., on a side of the control unit 62. Upon turning on the dermal injector, one or more of the following actions may occur: piston rod approaches change position (a sensor or switch may be used to recognize this state); syringe/needle carriage approaches change position (a sensor or switch may be used to recognize this state); LED is switched off; and cooling system is switched off. When the injection system is turned on, the display on the control unit 62 may indicate one or more of the following: injection volume and injection depth are set at fixed values, the selection is illuminated, e.g., in green light; trigger button LED on the injector is illuminated, e.g., in red light; the counters for total volume and number of injections are reset to zero. Although the injector system is turned on, it is not necessary the case that the cooling system is turned on. The cooling system may be turned on in a separate step.

Open the lid or flap of the hand piece. The flap may be opened upon activation of a flap switch. A trigger button LED on the injector may become illuminated, e.g., with a red light. Upon opening the flap, one or more of the following may subsequently occur: cooling system is turned off; piston rod approaches change position (a sensor or switch may be used to recognize this state); syringe/needle carriage approaches change position (a sensor or switch may be used to recognize this state). The injector is already in the change position at system start, as this position has been approached before switching off the system to remove the syringe. The cooling system is also switched off at system start.

After the flap has been opened, the operator inserts the manually ventilated syringe. Upon this insertion, the syringe detection switch may be activated (a sensor or switch may be used to recognize this state). After the syringe has been put in place, the flap is closed. The flap may be closed upon activation of a flap switch Upon activating the flap switch, one or more of the following may subsequently occur: the trigger button LED on the injector will become illuminated, e.g., in green light, only if a. maximum cooling temperature is reached (a sensor or switch maybe used to recognize this state), b. piston rod is lined up with the piston (a sensor or switch may be used to recognize this state), c. force sensor on the piston rod does not report any "overload" ("syringe empty") where a sensor or switch may be used to recognize this state, d. syringe/needle carriage is in the reference position (a sensor or switch may be used to recognize this state), e. cooling unit is present, f. syringe is detected (a sensor or switch may be used to recognize this state), g. flap is closed (a sensor or switch may be used to recognize this state). The following actions are only triggered if the presence of a syringe is recognized (a sensor may be used to recognize this state): a. cooling system is switched on, b. piston rod approaches the piston (a sensor may be used to recognize this state), c. syringe/needle carriage approaches reference position (a sensor may be used to recognize this state), d. LED is switched on.

Depending on the procedure, a second injection depth and/or a second injection volume may be selected. As before, the user selects one of three options for injection depth, and one of three options for injection volume. Upon selection, the option being selected will have a visual indicator, e.g., green lights will illuminate a visual display of the volume selected and the depth selected. These newly entered values or settings will be used at the next activation of the trigger button. A sequence in progress will use the value, which was valid at activation of the trigger button.

The injector portion of the hand piece is placed on the skin and the trigger button is pressed. Upon pressing the trigger button, a trigger button LED may become illuminated, e.g., in yellow light, until the cooling unit has reached the desired target temperature. The trigger button LED, located on the injector, may blink with a red light until the injection sequence is finished. Note that it should be checked whether an injection is still possible, even if the temperature of the cooling unit is not yet in the desired range.

Then the syringe empties. The hand piece may contain a force sensor on the piston rod to report any "overload", e.g., "syringe empty according to a sensor". The trigger button LED on the injector may become illuminated with a steady red light. In order for the syringe to empty its contents, the piston rod approaches the change position (a sensor may detect this) and in addition, the syringe/needle carriage approaches the change position (again, a sensor may detect this).

The syringe may be a 1-mL syringe, or it may be a 2-mL syringe, or it may be a 3-mL syringe, as three examples. The syringe preferably incorporates a Luer lock connection so that refilling is possible.

The control unit 62 should be easy to disinfect, and to that end, may have a simple construction with flat surfaces and few corners and edges.

It is also desirable that the injector may be placed on the control unit 62. To that end, the control unit 62 may comprise a docking station where the hand piece may be securely but reversibly rested. In other words, the dermal injector may include a docking station, and the control unit 62 may be incorporated into the docking station.

In one embodiment, the dermal injector is connected to or otherwise associated with a power supply. Two options of the present disclosure are an internal power supply and an external wall power supply or desktop power supply. An internal power supply may be preferred if, for functional reasons, the casing or other parts of the device must be grounded, i.e., connected to the protective earth. An internal power supply may be a preferred choice for large devices with high power consumption. In the present case, a solution with a wall power supply (power consumption of up to approx. 30 W) or a desktop power supply (like those for laptops or monitors) is a preferred embodiment as such power supplies can be bought fully certified. Such power supplies can also be bought with medical certification and adapters for the USA or Great Britain for an affordable price. In one embodiment, the device comprises a power supply adapter which provides a MSELV supply to the control unit 62.

The dermal injector device may incorporate an internal, rechargeable battery to make treatment easier. However, the power consumption, in particular that of the Peltier element, may be considerable. Also, as motors typically require a constant supply of power, the self-sufficiency is mainly dependent on the length of the session. One round of application may take about 5 seconds, and 400 applications therefore require a running time of approx. 2,000 seconds. With pauses, etc., a session therefore takes approx. 45-60 min. During this time, an average power of around 25 W is assumed (motors=8 W, Peltier=10 W, display=5 W, control=2 W). A battery pack with a 2 Ah capacity and an operating voltage of 22-24V makes battery-powered operation when not connected to the mains possible for approx. 2 hours. Accordingly, a battery pack is a viable option for powering the device of the present disclosure. Such a battery pack could use NiMH batteries, which measure approximately 150×55×30 mm and weigh approximately 650 g. Li-polymer batteries make smaller measurements and a lower weight possible, although, for safety reasons, they are not entirely simple to handle. Either type of battery, with suitable casing and wiring, may be added to the handle of the device of the present disclosure or may be present in the docking station.

Figure 15:
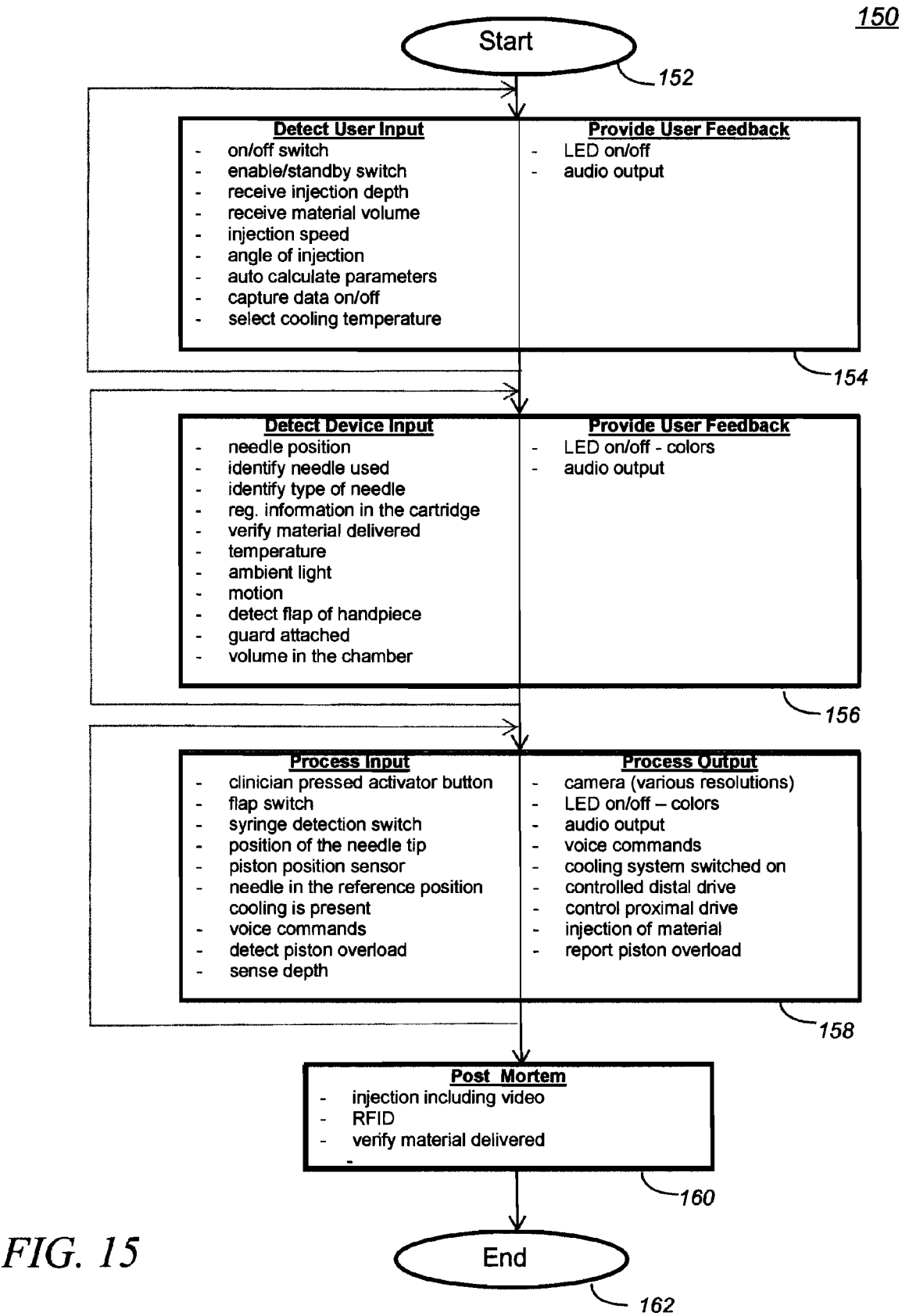
FIG. 15 is a data flow diagram illustrating a non-limiting process used by embodiments of a dermal injector.

FIG. 15 illustrates one implementation of a dermal injector which is controlled by a control unit 62. FIG. 15 includes a data flow diagram illustrating a non-limiting process 150 that may be used by embodiments of the dermal injector. In this regard, each described process may represent a module, segment, or portion of software code, which comprises one or more executable instructions for implementing the specified logical function(s). It should also be noted that in some implementations, the functions noted in the process may occur in a different order, may include additional functions, may occur concurrently, and/or may be omitted.

Processing in FIG. 15 begins at 152. At 154, the control unit 62 detects user input and provides user output via the control unit 62. The control unit 62 may be coupled via a wired connection or a wireless connection to the injection device 10. The control unit 62, via the coupling port 82 or another means, is able to detect the communicative coupling between the devices.

The control unit 62 detects an on/off switch, which may be via detection of power when the on/off switch directly controls power to the control device 62. Alternatively, the control unit 62 may exist in a low-power/sleep mode, and the on/off switch detects user input to wake the unit. Along these lines, the control unit 62 may have an enable/standby mode controlled by a switch. The control unit 62 will detect whether or not the control unit 62 is awake, ready for user input, or ready for use of the injection device 10. Alternatively, the control unit 62 may be in a sleep mode, wherein a display is dimmed, but nevertheless presents accurate information.

A reset input is provided in the control unit 62 to permit a user to reset some or all of the data collected by the control unit 62. In some embodiments, a single reset input will delete all of the data. In other embodiments, the reset input will permit various levels of data reset. For example, pressing a reset may permit a user to clear a first level of information; and pressing and holding the reset may permit the user to clear all of the information. Other scenarios are contemplated.

Throughout the user input detection process of 154, user feedback may be provided through LEDs, audio output, image output on a display, or some other output, such as tactile output. For example, pressing an on/off switch may illuminate a display, a bright LED, or some other user feedback. Providing a reset input may provide LED outputs having various colors to correspond to different levels of reset. Audio tones may also be used to indicate different levels of reset.

The on/off switch, enable/standby mode switch, and other user input may be detected by control unit 62 as discrete switch inputs, touchscreen inputs, programmatic inputs, motion inputs, or by some other input.

A user is able to provide additional input via the control unit 62. For example, as illustrated in FIG. 14, the user may provide needle depth input, material volume, needle speed, needle angle of injection, needle configuration (e.g., number of needles, needle pattern, size of needles, etc.) temperature of the cooling tip, and many other parameters. Other inputs are of course possible as discussed herein. FIG. 14 illustrates three levels of needle depth input, three levels of material volume input, and two levels of needle speed input. It is recognized that in some embodiments, the input is sequential and cycles through each of the available levels. It is recognized that in other embodiments, manual inputs such as needle depth, material volume, and needle speed, may be entered as ranges, numerical values, or in some other manner. Some embodiments of the dermal injector are intended for very intuitive use. Accordingly, the input is sequential, and the input is tied to immediate visual and tactile feedback (e.g., recognition of button press in a capacitive touchscreen, or via an electromechanical switch). In other cases, the dermal injector is intended for very sophisticated use. In these cases, the control unit 62 may include an elaborate user interface, and the ability to perform sophisticated algorithms for controlling a large plurality of injection parameters.

In some embodiments, the control unit 62 is arranged to calculate parameters of the dermal injector based on user input parameters. For example, if a user selects a material volume to be provided during an injection, the control unit 62 may detect a number and type of needles, and determine an appropriate needle speed. Along these lines, the control unit 62 may further arrange a method of injection delivery such that when the process is started by a clinician, the control unit will provide user feedback (e.g., audio, visual, tactile, and the like), to guide the practitioner during cooling of the injection site, advancement of the needle, and end of the injection, along with other parameters and indications.

At 156, the control unit 62 detects device input parameters and provides additional user feedback via LED's of various colors, audio devices, and the like. In some embodiments, the control unit 62 is able to determine whether a needle 24, the injector 14, or the housing 26 is in place. A clinician will be alerted if the injection device 10 is not ready for operation. The control unit 62 in some cases is able to determine whether a needle 24 has already been used. The used-needle detection reduces or prevents one patient from being contaminated by biological material of another patient. In this case, the control unit 62 may lock out the device from use until the needle 24 has been changed. In some embodiments, the control unit 62 is able to determine the type of needle used, including needle features such as the needle's length, diameter, orientation, structural material, the number of needles, and other like information.

In some embodiments, the control unit 62 is able to determine information about the cartridge 16 installed in the injection device 10. The control unit 62 is able to determine whether a cartridge is properly installed or installed at all. The control unit 62 may also be able to determine regulatory information about the cartridge such as material dosage information, lot number, date of manufacture, date of first use, last injection, number of doses remaining in the cartridge, and a wide variety of other parameters. Based on information from the cartridge, the control unit 62 may also be able to automatically adjust operational controls of the dermal injector. For example, the control unit 62 may automatically calculate needle depth, speed of injection, and the amount of material to be injected during one procedure. In still other embodiments, the control unit 62 is able to keep a computerized record of what material was injected, when the material is injected, the number of times the material is injected, the amount of material delivered, time/date information, and other information. In still other cases, the control unit 62 is able to associate a particular patient that will receive, or has received, an injection with the specific information associated with that injection as described herein. In this way, the control unit 62 may be able to verify that material delivered to a patient is medically approved for the patient.

Prior to an injection, the control unit 62 may retrieve information from environmental sensors 76. The information may include temperature at the cooling tip or in proximity thereof, ambient light, whether the injection device 10 is in motion, whether a hand-piece flap or some other portion such as the lower guard 12 of the injection device 10 is out of place.

At 158, the control unit 62 may monitor an injection procedure. Also at 158, in some embodiments, the control unit 62 may direct the injection procedure.

When presented with suitable feedback, a clinician may press the activator button 58 on the injection device 10. The control unit 62 will detect the activator button 58 press, and in some cases, the control unit 62 will commence an injection operation.

Various exemplary operations to perform injections are described in the present disclosure. It is recognized that acts in the various procedures appear in different order, are omitted, and other acts are added. From the procedures described, an understanding of the operation of the dermal injector is provided. When the control unit 62 detects a clinician's input to perform an injection, embodiments of the control unit 62 receive input data from one or more sensors and provide output data to one or more other sensors to carry out the acts as illustrated.

The control unit is arranged with sensors to recognize the position of the needle 24 tip within various positions in the guard chambers 34, 36, 38. The control unit 62 will recognize the needle tip being in a reference position, and the needle tip being advanced through the service position. The control unit 62 will also recognize the injection of material, stress on the injection piston, or overload thereof, and input from other sensors. The sensor data received through the environmental sensors 76 to the control unit 62 works cooperatively with output signals provided to control distal drive 42 and proximal drive 44. As distal drive 42 and proximal drive 44 are directed, the needle 24 is advanced and retracted appropriately to deliver the determined material dosage at the determined material speed. In some cases, the control unit 62 receives voice commands from the clinician rather than manual input commands. In some cases, the control unit 62 provides voice commands to direct the clinician through proper operation of the dermal injector.

Each of the operations at 154, 156, and 158 may be performed once or may be performed many times. In some embodiments, the process 150 operates as a state machine wherein input information received by the control unit 62 from a user or a sensor will direct advance or retreat to one state or another.

After an injection, processing in some cases falls through to 160. At 160 a postmortem of the injection may be conducted. In cases where a user has enabled a camera device 74, video from before the injection, during the injection, and after the injection may be recorded and reviewed. In cases where an RFID, barcode, or other communication device 84 is present, information may be gathered or otherwise communicated between the injection device 10 and the control unit 62. The information communicated may include specific information for practitioners or service providers regarding the material delivered in the dosage. Operational characteristics of the dermal injection device may be communicated. In yet other embodiments, specific information related to the particular patient that received the injection in cooperation with information directed to the injection itself may be communicated.

The processing of 150 ends at 162.

In one embodiment of the present invention the injection device achieves an injection which is completely manually operated and not powered by electricity. Alternatively, the device may be powered by electricity or a battery. When a battery is employed, preferably a replaceable or rechargeable battery, then the device is wireless, i.e., there is no need for a power cord.

Further preferred, the injection device may be driven by hydraulic means, such as a hydraulic pump. In one embodiment the hydraulic means are not included in the injection needle housing but are provided outside of the injection device. Accordingly, in this case the hydraulic means are a hydraulic pump that is optionally provided that is located on the floor and can be operated by foot. This provides the advantage that the injection device is reduced in size and weight.

In a further optional embodiment the injection device of the present invention comprises two, three, four, five or more injection needles, for example, six, seven, eight, nine, ten, eleven and twelve needles. Preferably, it is optionally provided that all injection needles are injected simultaneously. However, it another embodiment, it is optionally provided that not all of the injection needles are injected simultaneously. For example, the different injection needles can be injected independently in a distinct depth with a distinct angle.

A needle as mentioned herein may be a microneedle, i.e., a relatively short and thin needle. For example, in the treatment of scarring, such as may occur from acne, a needle length of 1.4-2.1 mm is often suitable, although the precise needle should be selected based on the depth of the scars themselves. As another example, in an anti-aging treatment such as wrinkle removal, a needle length of 0.4 to 1.1 mm is often suitable in order to reach the dermis layer of the skin.

The needle arrays which are part of the device as disclosed herein may consist of multiple needles or multiple microneedles. These needles may be solid or biodegradable (i.e., the needle dissolves in the body after an injection has occurred). So-called solid needles are made from non-degradable material such as metal (e.g., stainless steel, titanium) or glass, and they may have a hollow center. Degradable needles may be made from sugar or sugar derivatives (e.g., polymers made from lactic acid and/or glycolic acid). Degradable needles provide the advantage of eliminating sharp waste, since they degrade within minutes after an injection has been performed. In one embodiment, the needle is a non-degradable needle. In another embodiment, the needle is a degradable needle. In one embodiment the needle is a microneedle, which may be degradable or may be non-degradable.

In a further preferred embodiment of the invention the guard (12) has a round or horseshoe-shaped form. Further shapes may be applicable for a skilled person. Preferably, it is optionally provided that the guard is constructed to provide an opening for the injection needle. In a further optional embodiment of the present invention, the guard includes several openings which allow the passing through of several injection needles during the injection.

In one embodiment the guard may be surrounding the injection needle during the injection. Preferably, the guard may include a Peltier element which provides cooling in deeper injection regions, such as muscle tissue or tissue which is adjacent to tendons. The presence of a Peltier element as part of the guard, or in the tip of the hand piece when a guard is not present, cools the skin in the area of the injection site to achieve local or regional cryoanesthesia, sometimes referred to as refrigeration anesthesia, and therefore reduces the patient's sensation of pain. In a one embodiment of the present invention it is optionally provided that the guard is a head section with an opening.

In a preferred embodiment, the injection device of the present invention achieves an injection in the desired tissue layer to an injection depth in the range from 0.5 mm to 5 cm, 0.5 mm to 4 cm, 0.5 mm to 3 cm, 0.5 mm to 2 cm, 0.5 mm to 1 cm, 0.5 mm to 5.5 mm, preferably in a depth from 1.5 mm to 4.0 mm, more preferably in depth from 2.0 mm to 3.5 mm, most preferably in a depth of 3.4 mm. The injection depth is dependent on the distinct application. For example, the injection depth is preferably 3.4 mm in the case of DSC cell injection. In the case where fibroblasts or adipocytes are injected, the injection depth is preferably about 5.0 mm. Preferably, adipocytes may be used as a so called "filler" and injected to a depth which corresponds to a subcutaneous injection. Further, adipocytes may be injected to depth of about 3 to 4 mm. Preferably, injections into muscle tissue or in tendons may be conducted to a depth of about 2 cm to 3 cm up to 5 cm. The injection depth may be determined in part by the length of the injection needle and by the angle of the injection.

It is included within the experience of a person skilled in the art to apply the respective injection depth dependent on the distinct type of substance and dependent on the desired application form and effect which should be achieved. Preferably, the injection volume is applied in a constant manner during the retraction movement.

In a further embodiment of the present invention, it is optionally provided that different injection volumes are injectable with different injection depths during the retraction movement of the injection needle. Accordingly, preferably a first distinct volume is injected in a first site of, for example, 5.5 mm depth, then during the retraction movement of the injection needle a second volume is injected in a depth of, for example, 3.4 mm. Accordingly, in a preferred embodiment it is optionally provided that the volume in the region which is treated during the injection is subdivided in different injection depths and during the retraction movement distinct volumes are injected in each of the injection depths.

In a further preferred embodiment, the void volume of the injection is very small so that all or nearly all of the liquid contents of the chamber are delivered to the subject and little or no liquid remains within the device after the injection. In various embodiments, the void volume is no more than 10 μL, or no more than 20 μL, or no more than 30 μL, or no more than 40 μL, or no more than 50 μL, or no more than 60 μL, or no more than 75 μL, or no more than 100 μL (0.5 mL), or no more than 200 μL, or not more than 500 μL, or no more than 750 μL, or no more than 1000 μL (1 mL).

In a preferred embodiment of the present invention it is optionally provided that the injection device allows the application of different injection forms. Preferred injection forms are a bolus injection, an injection in a tadpole-like form, a continuously distributed injection over the length of the injection path with the application of the same volume during the retraction movement, or a combination of different injection forms. The injection volumes can be varied at each distinct injection site of the distinct injection depth.

The range of the injection length defines the length of the injection path during the retraction movement of the injection needle. Accordingly, it is optionally provided that the total injection length is defined by the length of the injection needle. Preferably, it is optionally provided that the total injection length of the injection needle is in a range from 2.0 mm to 20 mm, preferably from 5.0 mm to 15 mm, more preferably about 10 mm.

In a preferred embodiment of the present invention, the angle between the injection needle and the guard is adjustable. Optionally, the angle between the injection needle and the application element is in the range from 10 degrees, to 90 degrees, 10 degrees to 80 degrees, 10 degrees to 70 degrees, 10 degrees to 60 degrees, 10 degrees to 50 degrees, 10 degrees to 40 degrees, preferably from 15 degrees to 25 degrees, more preferably 20 degrees. In a preferred embodiment of the present invention, it is optionally provided that the angle between the injection needle and the guard and/or the injection depth allow dermal application of the liquid.

Accordingly, the injection device of the present invention allows conducting the application of a substance, like a liquid, such as cells in a liquid medium, in a preferably constant manner with a fixed angle and a defined depth for each injection site. The application of a substance and in particular of cells, like DSC cells, in the scalp of a subject, has to be conducted in the dermal layer as particular tissue layers. Further application forms, such as injections in muscle tissue or in tendons require the injection within deeper layers. This is achieved with the injection device of the present invention which allows the injection with a defined angle and a defined depth which remains constant during each single injection.

In one preferred embodiment of the present invention, the injection device provides an angle of 20 degrees in combination with an injection depth of less than 1 mm for the application of, e.g., fat cells into a subject.

In another preferred embodiment of the present invention, the injection device provides an angle of constant 90 degrees in combination with an injection depth of at least 1 cm for the application of a substance into, e.g., tendon cells. Optionally, the determination of the necessary injection depth is monitored by ultrasound.

It is optionally provided with the injection device of the present invention that distinct injection angles are combined with distinct injection depths. Accordingly, it is optionally provided that desired combinations of distinct injection angles with distinct injection depths can be adjusted with the injection device of the present invention. Preferred combinations of injection angles with injection depths are 20 to 30 degrees with 1 mm to 1 cm, 30 to 40 degrees with 1 mm to 1 cm, 40 to 50 degrees with 1 mm to 1 cm, 50 to 60 degrees with 1 mm to 1 cm, 60 to 70 degrees with 1 mm to 1 cm, 80 to 90 degrees with 1 mm to 1 cm.

In a preferred embodiment of the present invention, the diameter of the injection needle(s) is in the range of 18 to 32 G, of 20 to 30 G, more preferably 24, 25 or 26 G. 26 G has a diameter of about 0.46 mm.

In a further preferred embodiment a syringe with a volume of 1 ml is used within the injection device of the present invention. Preferably, such a 1 ml syringe allows 6 injections of 166 μl. Syringes with 2, 5 or 10 ml may also be utilized, for example. Further, syringes with a bigger or smaller volume may also be used in optional embodiments of the present invention depending on the particular use of the injection device.

Preferably, it is optionally provided that the opening of the injection needle is adjusted in an upward direction. According to the present invention an upward direction means that the orientation of the injection needle is directed towards the surface or region where the injection occurs. This provides the advantage that the cells can be applied in an optimal orientation within the distinct tissue layer. In the case where the injected cells are, for example DSC cells, an injection in an upward direction in the dermal layer is advantageous since the cells can more easily grow in the direction of the scalp. Thus, the outgrowth of hair is promoted with the injection of DSC cells into the scalp of a subject with the injection device of the present invention.

Preferably, the injection device is further comprised of means for lighting. Such lighting may be, but is not restricted to, LED (light-emitting diode) or other lighting appliances. The provision of lighting appliances allows a better visualization and an easier determination of the distinct injection site. In a further preferred embodiment of the present invention, the means for lighting are included in the handle or in the guard, such that the injection site is illuminated.

In a further preferred embodiment of the present invention, it is optionally provided that further appliances, such as optic devices or a laser device is included in the injection needle housing. Preferably, the optic device is a camera, such as a video camera or a photographing apparatus.

In one embodiment the injection device comprises a guard with fastening means for fastening the injection device to the subject. In a preferred embodiment of the present invention the fastening means comprise the application of a vacuum. In one embodiment of the present invention, the fastening means include glue or a fixation frame.

In a further embodiment, it is optionally provided that the injection device of the present invention comprises a laser device. The laser device allows the projection of marked site for the injection on distinct sites of the surface, where the injection should be conducted. Further preferred it is optionally provided that the laser device provides the projection of several marked sites, where the injection should be conducted. The marked sites from the laser device provide the advantage that the distance between the different injection sites can be constantly maintained. In a further preferred embodiment of the present invention, the use of one, two, three or more sources of a laser is provided. The provision of a laser has further the advantage that this laser can have an alternative penetrative function in comparison to the injection needle. Further, the laser provides the advantage that bleeding during the injection is inhibited or at least reduced. Furthermore, in a preferred embodiment of the present invention, it is optionally provided that the laser is used in combination with the injection needle. Thus, it is preferably optionally provided that the injection region is prepared with the laser. Due to this preparation, an injection channel can be formed wherein then the injection with the injection needle can be performed. While a laser is a feature of one embodiment of the present device, the laser is an optional feature.

In a further optional embodiment, the guard, the injector and the cartridge are exchangeable. Accordingly, it is possible that for each subject the items can only be used individually and then can be changed individually to fulfill hygienic standards.

Optionally, the construction of the injection device of the present invention inhibits that the user of the device may be unintentionally hurt by the injection needle since the needle is retracted within the injection needle housing during its starting position, or there is a guard present around at least some sides of the needle head. Thus, the injection needle is not exposed all the time.

In one embodiment the present disclosure provides an injection device which allows the precise and targeted delivering of material, such as cells, into a subject, such as the dermal tissue layers of a subject. An improved delivery of cell-based products is provided by the device of the present disclosure, which in turn improves treatments for both aging and sun damaged skin as well as pattern baldness, among other methods as disclosed herein. The device of the present disclosure may be used in cell therapies that are designed to treat chronic tendinosis, damaged or aging skin, and pattern baldness, as three examples. Healthy cells may be isolated from the patient himself (or herself) and then reintroduced into the patient at a desired location using the device of the present disclosure. For example, healthy hair follicles may be isolated from a patient and then reintroduced into another location on the scalp using the device of the present disclosure.

An exemplary dermal injector of the present disclosure may provide injection volume settings selected from, for example, 20 µL, 25 µL, 30 µL, 35 µL, 40 µL, 45 µL, 50 µL, 55 µL, 60 µL, 65 µL, 70 µL, 75 µL, 80 µL, 85 µL, 90 µL, 95 µL, 100 µL, 105 µL, 110 µL, 115 µL, 120 µL and 125 µL. There may be some variation in the precise amount of material that is delivered, where that variation may be, for example, +/−2 µL or +/−3 µL, +/−4 µL, +/−5 µL, +/−6 µL or +/−7 µL. For example, the injector may provide injector volumes between 40 and 100 µL, or from 50 to 90 µL. The dermal injector may have a number of selectable setting, such as three selectable settings, or four selectable settings. As one embodiment, the dermal injector has three selectable application volumes, which are 50 µL, 70 µL and 90 µL.

An exemplary dermal injector of the present disclosure may provide penetration depth setting selected from 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm and 3.5 mm. There may be some variation in the precise penetration depths, where that variation may be selected from 0.07 mm, or 0.08 mm, or 0.09 mm, or 0.1 mm, or 0.11 mm, or 0.12 mm, or 0.13 mm, or 0.14 mm, or 0.15 mm. The dermal injector may have a number of selectable penetration depths, such as three selectable setting, or four selectable settings. As one embodiment, the dermal injector has three selected penetration depth settings, which are 0.5 mm, 2.0 mm and 3.0 mm.

In order to assure a desired penetration depth, the distance from the tip of the needle(s) to the base of the guard/cooling unit should be a known and constant value. In one embodiment, that value lies within the range of 1 and 3 mm, when the needles are in the fully retracted, reference position. In one embodiment, the needles protrude from their holder by no more than a known and constant value, in order to assure that the needle(s) can extend into the patient by no more than that value. In various embodiments, the needles protrude from their holder by no more than 6 mm, or no more than 5 mm, or no more than 4 mm.

In one embodiment, a dermal injector of the present disclosure comprises a power supply adapter, a control unit, an injector device comprising a motor unit and a cooling unit, and disposable parts comprising a) a needle with a syringe holder and a female Luer lock interface; and b) a syringe with a removable handle and a male Luer-lock interface. Any of the dermal injector embodiments as disclosed herein may have a) a needle with a syringe holder and a female Luer lock interface; and b) a syringe with a removable handle and a male Luer-lock interface.

The dermal injector may comprise one or more sensors. For example, it may contain a sensor which detects the temperature at the tip of the cooling unit. In addition, the dermal injector may be programmed so that the needles will not move to the injection position unless the temperature at the tip of the cooling unit reaches a pre-set value, such as 8° C. or 6° C. As another example, it may contain a sensor which indicates the location of the cooling unit relative to the location of the movable syringe holder. As yet another example, the dermal injector may contain a sensor that indicates that the tip of the thread bar has reached the piston of the syringe. As still another example, there may be a sensor present that will detect an emptied syringe. Still another example is that the dermal injector may have a sensor which indicates that the syringe carriage is in the change position, which is the rearmost position of the carriage. Also, there may be a sensor which indicates that a syringe has been inserted into the syringe compartment of the handle of the injector device. There may also be a sensor that indicates that the lid or flap of the syringe compartment has been closed. The dermal injector of the present invention may comprise any one or more of these listed sensors.

In addition, the present disclosure provides methods of delivery for substances, which methods may be achieved with embodiments of the dermal injector or injection device described herein. Reference to dermal injector shall include reference to the injection device, and reference to the injection device shall include reference to the dermal injector, unless the context clearly indicates otherwise. For example, the present disclosure relates to the use of the dermal injector and the injection device of the present disclosure for the application of a substance, such as a liquid, into the tissue of a subject. In one embodiment, the tissue is skin and the application is a dermal treatment. In another embodiment, the tissue is the scalp and the application is a scalp treatment. In still another embodiment, the tissue is dental tissue and the application is a dental treatment. In yet another embodiment, the application is an orthopedic treatment, and the tissue is any one or more of the skeletal system and associated muscles, joints, tendons and ligaments. These are exemplary embodiments of the methods of the present disclosure.

In a preferred embodiment of the present invention the substance is selected from the group consisting of cell suspension, gel-like materials, therapeutic substances, cosmetic substances, and diagnostic substances.

Cosmetic substances can include, but are not restricted to application of adipocytes as filler, the application of hyaluronic acid, or application of botulinum toxin (Botox, Btx) in the wrinkle treatment.

Therapeutic substances can include, but are not restricted to, antibiotics, anesthetics, analgesics, vaccines, antibodies.

In a preferred embodiment of the present invention it is optionally provided that the cell suspension is mixed with growth factors. In a further preferred embodiment of the invention it is optionally provided that the cell suspension is included in a gel-like structure. Preferably, such gel-like structures represent mixtures of extracellular matrix proteins which mimic the extracellular environment of distinct tissues. Further preferred is a gel-like structure such as hyaluronic acid.

Accordingly, preferably the dermal injector or injection device of the present invention is used to deliver cells in a suspension or in a liquid medium to a subject.

In a preferred embodiment of the present invention, it is optionally provided that the dermal injector or injection device is used for the application of a substance into a distinct tissue of a subject. In particular, it is preferably optionally provided that the injection device is used for the application of cells into the skin, preferably as cell suspension, in the treatment of hair loss, alopecia, such as alopecia areata, or other symptoms associated with a lack of or too less hair. Further, the injection device of the present invention is preferably used for the application of a liquid such as a medicament, a cytokine or a growth factor into a subject. Preferably, this application of the liquid into a subject is conducted in connection with the treatment of hair loss, alopecia, such as alopecia areata, or other symptoms associated with a lack of or too less hair. In a further preferred embodiment of the present invention, the injection device is used for the application of a substance into a muscle of a subject. Further preferred, the injection device is used for the application of a substance into a tendon of a subject. Further preferred, the injection device is used for the application of a substance into fascia of a subject. Further preferred, the injection device is used for the application of a substance into the joint of a subject. Further preferred, the injection device is used for the application of a substance into the cartilage of a subject. Further preferred, the injection device is used for the application of a substance into the submucosal tissues of a subject.

Thus, the dermal injector or injection device may be used for intradermal injection. An intradermal injection provides for an injection of material into the dermis, which is one of the layers of the skin, below the epidermis. The device may also be used for an injection of material into the epidermis. The device may also be used for subcutaneous injection, where an injection of material is made into the fat layer between the skin and muscle. Examples of suitable locations for a subcutaneous injection include the abdomen, the thigh, the lower back, and the upper arm. The device may also find use in intramuscular injection, wherein an injection of material is made directly into muscle tissue. Examples of suitable muscle tissue include the thigh muscle, e.g., the vastus lateralis muscle, the hip muscle, e.g., the ventrogluteal muscle, the upper arm muscle, e.g., the deltoid muscle, and the buttocks, e.g., the dorsogluteal muscle. Each of these different locations provides a separate embodiment of the methods of the present disclosure.

For a method of the present disclosure that entails intradermal or epidermal injection, the following are examples of material that may be injected. In one embodiment, hyaluronic acid is injected. In another embodiment, collagen is injected. In yet another embodiment, fat is injected. In still another embodiment, elastin is injected. In another embodiment, poly-L-lactic acid is injected. In yet another embodiment, polymethylmethacrylate beads are injected. In still another embodiment, platelet rich plasma (PRP) is injected. In one embodiment, collagenase (particularly useful for treating burns, keloids and Dupuytren's disease) is injected. In yet another embodiment, growth factors (particularly useful when administered post-surgery) are injected.

The intradermally or epidermally injected material may be a drug or a biologic. In one embodiment, glutathione (particularly useful for skin whitening) is injected. In another embodiment, ascorbic acid (particularly useful for skin whitening) is injected. In yet another embodiment, hair follicle derived cell solutions such as melanocytes (particularly useful for seeding treatments for vitiligo) are injected. In still another embodiment, non-bulbar dermal sheath cells are injected. In another embodiment, fibroblasts are injected.

In another embodiment, dermal sheath cups are injected. In yet another embodiment, an anti-inflammatory drug is injected. For instance, the anti-inflammatory drug may be a corticoid steroids for use in treating inflammatory skin diseases For a method of the present disclosure that entails subcutaneous injection, the following are examples of material that may be injected. In one embodiment, fat grafting is performed. A fat grafting procedure transfers fat from areas in which a person has excess fat, such as the outer thighs, and injects it into areas that may be lacking in volume, such as the person's face, hands, breasts or buttocks. Fat grafting is also called autologous fat transfer. After liposuction removes the fat from the over-fatty area, the tissue is processed into a liquid and injected into the area that is lacking in volume. Another form of fat grafting, called lipofilling, may be used to fix minor differences in the shape, balance, or position of the reconstructed breast compared to the other breast.

In another embodiment, subcutaneous injection may be used to deliver drugs or biologics. Examples include Procrit and Velcade. Procrit (epoetin alfa) is a man-made form of a protein that helps the body produce red blood cells. The amount of this protein in your body may be reduced when you have kidney failure or use certain medications. When fewer red blood cells are produced, you can develop a condition called anemia. Procrit is used to treat anemia (a lack of red blood cells in the body) in patients with Chronic Kidney Disease (CKD). Procrit is also used to treat anemia caused by zidovudine in HIV-infected patients and in certain patients receiving chemotherapy. Velcade, also known as bortezomib, may be used in the treatment of cancer, such as multiple myeloma. The device of the present disclosure may be used to treat lesions, e.g., cancer lesions, by intra-lesional injection of therapeutic substances.

In another embodiment, subcutaneous injection may be used to achieve mesotherapy. Examples of mesotherapy which may be achieved by methods of using the device of the present disclosure include the delivery of phosphatidylcholine, T3-T4 thyroid, isoproterenol, aminophylline, pentoxifylline, L-carnitine, L-arginine, hyaluronidase, collagenase, yohimbine, co-enzyme cofactors, dimethylethanolamine, gerovital, glutathione, tretinoin, alpha lipoic acid, vitamin C, procaine, lidocaine, *Ginkgo biloba*, melilotus, C-adenosine monophosphate, multiple vitamins, trace mineral elements, carbon dioxide, and mesoglycan.

As mentioned previously, the dermal injector or injection device as disclosed herein may be used in orthopedic treatment. As one example, the orthopedic treatment may be a treatment for osteoarthritis. In another example, the orthopedic treatment is a treatment for tendonitis. In one embodiment, the device is used in a method that delivers adipose-derived mesenchymal stem cells as an orthopedic treatment. In another embodiment, the device is used in a method that delivers amniotic stem cells as an orthopedic treatment. In another embodiment, the device is used in a method that delivers platelet rich plasma (PRP) as an orthopedic treatment. The adjustable volume of the injector of the present disclosure is well suited for cellular or PRP orthopedic treatments, as a precise dosage (i.e., the cell number) can be administered at each injection, minimizing potential technical errors that may be caused by a clinician.

As mentioned previously, the dermal injector or injection device as disclosed herein may be used in dental treatment. For example, the device may be used in a method for local injection of anesthesia. When injecting anesthesia for dental treatments, it is important to have minimal wobbling as the needle enters the patient's dental tissue in order to minimize pain and discomfort felt by the patient. Another factor that may cause discomfort is the rate of fluid infiltration into the tissue. The device of the present disclosure both minimizes needle wobble and allows highly controlled delivery rate of anesthesia. A rate of delivery can be selected and maintained which is below a threshold that causes discomfort.

As mentioned previously, the dermal injector or injection device as disclosed herein may be used in scalp treatment. For example, the device may be used in a method for delivering corticosteroids to the scalp, e.g., to treat alopecia areata. In this method, the corticosteroid is delivered to the area of the scalp that is showing hair loss, e.g., 80 injections may be made in the affected area. As another example, the device may be used in a method for delivering platelet rich plasma (PRP) to an area of the scalp, e.g., to treat androgenetic alopecia. In this method, the PRP is delivered to the area of the scalp that is showing hair loss, e.g., PRP may be injected at a concentration of 0.1 mL PRP per square centimeter of affected scalp area. The multi-needle device of the present disclosure allow for faster and more controlled administration of the drug product, which is especially useful when treating large areas.

As mentioned previously, the dermal injector or injection device as disclosed herein may be used to inject material into a subject's skin. In one embodiment, the present disclosure provides a method of treating chronic skin disorders by administering a therapeutically effective amount of an active agent. Exemplary skin disorders include skin cancer, lupus, rubeola, acne, hemangioma of skin, cold sore, psoriasis, rosacea, seborrheic eczema, hives, vitiligo, warts, necrotizing fasciitis, cutaneous candidiasis, carbuncle, cellulitis, hypohidrosis, impetigo, cutis laxa, decubitis ulcer, erysipelas, dyshidrotic eczema, canker sore, herpes stomatitis, ichthyosis vulgaris, dermatomyositis, molluscum contagiosum, acrodermatitis, sebaceous cyst, seborrheic keratosis, pilonidal sinus, keloid, lichen planus, actinic keratosis, stasis dermatitis, eczema, tinea versicolor, pemphigoid, mouth ulcers and shingles. Other dermal treatments may be used to treat planter fasciitis, alopecia, non-chronic skin disorders, burns, warts and skin cancers. The device may also be used to delivery adrenaline or epinephrine to offset an allergic reaction to, e.g., a bee or wasp sting.

Various patches may be used to delivery drugs to the dermis. Examples include patches with time-released drugs as contraceptives and for anti-smoking. As a replacement for such patches, the present disclosure provides a method of using the dermal injector or injection device as disclosed herein, to deliver such drugs.

The dermal injector or injection device may be used to provide an injection for vaccination. The injection may be into the epidermis, the dermis, or it may be delivered intramuscularly or subcutaneously. For instance, the present disclosure provides a method of vaccination against each of chickenpox, diphtheria, Hib, hepatitis A, hepatitis B, flu, measles, mumps, pertussis, polio, pneumococcal, rotavirus, rubella, and tetanus by delivering the appropriate antigen, optionally in combination with an adjuvant.

The dermal injector or injection device may be used to provide an intradermal injection for gene therapy. For example, siRNA/shRNA may be delivered to the skin for genetic skin and hair modification. In one embodiment, the device is used in a method for gene therapy.

The dermal injector or injection device may be used to deliver botox to the epidermis or may be used to deliver botox to the dermis. Botox is used, for example, to reduce the presence and visibility of wrinkles, as well as to reduce the activity of sweat glands, among other purposes.

Dermatologists have been frustrated for years by the lack of a precise injector to deliver currently approved dermal fillers into the broad potential markets for fine wrinkles of the face, décolleté, and hands. The injector device of the present disclosure addresses these unmet needs by enabling precise and repeatable delivery of injectable substances. The injection device of the present disclosure provides superior control over injection consistency while also enabling less skilled clinicians to undertake these procedures with the desired results. This may significantly expand the number of dermal injection procedures currently performed—in particular, cosmetic injectables. As an example, the US hyaluronic acid (HA) market is currently valued at over US$1 billion per year and growing in excess of 10% per year. This market primarily serves dermal areas that address deep facial wrinkles and folds but does not adequately address fine wrinkles. The device of the present disclosure, which is capable of delivering a controlled injectable, utilizing a multi-head configuration, and that eliminates the need for delivery of a local anesthetic, may increase the HA market into areas including the fine wrinkles of the face, the hands and the décolleté.

The dermal injector or injection device may be used to deliver agents to the skin for superficial wound healing. Such agents may accomplish one or more of enhancing the proliferation of cells, the migration of cells, and the acceleration of the healing of wounds. Human cell-conditioned media developed in embryologic-like conditions may be delivered. Fetal tissue may be beneficially delivered due to the unique characteristics of fetal epithelial and mesenchymal cells and the functioning of the fetal immune system. Transforming growth factor, e.g., (TGF)-β3 may be applied during the healing of wounds. Agents such as platelet-rich plasma (PRP) and erythropoietin (EPO) are modulators that have a positive effect on tissue regeneration and have been used successfully to enhance the healing of wounds. Both the peptide growth factors and the lipid fraction of PRP may be delivered by the device of the present disclosure.

For example, the dermal injector or injection device may be used in a method for delivering dermal filler such as hyaluronic acid, adipose tissue or a combination thereof. As another example, the device may be used in a method for delivering platelet-rich plasma (PRP), which acts to stimulate collagen production, as well as keratinocyte and fibroblast proliferation. The injection of PRP may also serve to promote angiogenesis and thereby facilitate tissue regeneration. The delivery of PRP to skin may be used in a method for anti-aging, i.e., to remove/reduce wrinkles and smooth out skin, as mentioned above. The delivery of PRP to skin may also be used to treat stretch marks, such that they become less noticeable. In another embodiment, PRP is delivered via a device of the present disclosure to treat acne marks or scars, and make them less noticeable. In another example, the device as disclosed herein may be used in a method for delivering glutathione, which is an anti-oxidant that reduces formation of melanin and leads to paler (whiter) skin. Thus, the present disclosure provides a method of lightening skin using a device as disclosed herein. In yet another example, the device as disclosed herein may be used in a method for delivering kenalog or corticosteroid for treating a keloid. A keloid refers to a scar which forms as a result of over-production of type III collagen at the site of an injury, and is eventually replaced by type I collagen. The present disclosure provides a method of treating a keloid so that it becomes less noticeable.

The dermal injector or injection device of the present disclosure provides for injecting, i.e., any of administering, infusing, introducing or otherwise delivering, via an electrically powered drive system which controls the depth, rate of deposition, and the area of disbursement via different blunt or sharp needle head configurations such as a single, parallel numbers or square or rectangular configurations of needles. The programmable depth and volume of the delivery device of the present disclosure allows for precise and consistent administration of fluid at each application, equally distributing the drug product in the treatment area. In addition, the cooling element of the injector removes the need for anesthetic usage for these treatments. The substance being injected is delivered to the tissue during the retraction movement of the needle thereby minimizing any sheer force on the substance being injected.

In one aspect the present disclosure provides a method of delivering material into a patient by use of a needle or a plurality of needles. The needle or needles penetrate the patient, and the material is passed through a needle, then ejected out the end of a needle, and then into the patient, i.e., into the patient's tissue. Prior to entering a needle, the material may be held in a chamber, also referred to as a cartridge, where the chamber is in fluid communication with a needle. For example, the chamber may be a syringe including a barrel, where the barrel fits tightly within the chamber.

In one embodiment of a method as disclosed herein, the method includes using a plurality of needles to deliver material into a patient. When a plurality of needles are used, then the members of the plurality function similarly. In other words, each needle in the plurality penetrates into the patient at the same time and by the same distance to deliver the same material and the same amount of the material to the patient. Each member of the plurality may receive material from a single chamber that holds a reservoir of material to be injected. The dermal injector of the present invention is configured so that it may include a single needle or a plurality of needles. In a preferred embodiment, the needle or needles are attached to a standard shaped housing, and this standard housing may be reversibly attached to the injector device and thereby place the needle or needles into fluid communication with the chamber that holds the reservoir of material. The housing is considered to be standard in that the housing attaches to the injection device regardless of the number of needles that are attached to the housing. Thus, the clinician may have a set of housings, each with a different needle head, e.g., a different number and/or size and/or length of needles, and the clinician may select from this set in order to obtain the best choice of needle(s) for the particular process being performed.

In one embodiment of a method as disclosed herein, the method includes cooling the surface area of the patient that will be penetrated by the needle or needles. This surface area may be referred to as the first surface area. The cooling may be accomplished by contacting an adjacent surface area, i.e., a surface of the patient which is adjacent to the surface that will be injected, where this adjacent surface may be referred to as the second surface area. When the second surface area is cooled, that cooled second surface area will draw heat from the first surface area with which it is in contact. The dermal injector of the present invention is configured so that it may include a cold surface which is near the needle or needle array of the dermal injector. This cold surface may be brought into contact with a surface (the second surface area) of the patient to be injected, in order to draw heat away from the surface (the first surface area) of the patient to be injected and thereby reduce discomfort associated with the passage of the needle(s) into the patient.

In one embodiment of a method as disclosed herein, the method includes depositing material in the patient using the needle or needles as described herein. In a preferred method, the material is deposited while the needle or needles are being withdrawn from the patient. As discussed elsewhere herein, it is advantageous to deliver material while the needles are being withdrawn from the patient, rather than, for example, deliver material while the needle is in a static position, i.e., while the needle or needles are not moving relative to the surface of the patient, or while the needle or needles are being inserted into the patient. The dermal injector of the present invention is configured so that material may be delivered during the time when the needle(s) are being withdrawn from the patient.

In one embodiment of a method as disclosed herein, the method includes multiple injections, each injection being performed with one or a plurality of needles, the multiple injections being temporally distinct from one another, and optionally also being spatially distinct from one another. In other words, a method of the present disclosure includes injecting material more than once, e.g., twice, three times, four times, five times, etc. up to 20, or 25 or 30, or 35 or 40, or 45 or even 50 or more times, into a single patient. Each distinct injection occurs at a different time and optionally is also made at a different location on the patient, relative to the previous injection. The dermal injector of the present invention is configured so that the different injections are consistent in terms of the depth beneath the patient's surface that material is being deposited, and the amount of material that is deposited during each injection. Due to the fixed spatial arrangement of a plurality of needles attached to the housing, each injection is also consistent in terms of the surface area of tissue that is receiving material. When the material is ejected from the needle while the needle is being withdrawn from the patient, each injection provides for a volume of patient tissue to receive the material. Thus, in one embodiment, the dermal injector of the present invention provides a consistent volume of patient tissue that receives the material being injected, where that volume is consistent across multiple injections.

For example, the present disclosure provides a method comprising:
a. selecting a first exterior surface of skin of a patient, the first surface comprising a surface area and a first average temperature;
b. cooling the first surface to a second average temperature;
c. penetrating the first surface with a plurality of needles, the plurality of needles extending from the first surface by a uniform distance into the patient;
d. withdrawing the plurality of needles from the patient while also ejecting a material out of the needles and into the patient; and
e. repeating steps a, b, c and d to deliver additional material to the patient.

The first exterior surface of skin refers to any surface of the skin which is accessible to the tips of the needle(s) when the needles first enter the subject. Thus, the epidermis layer of skin that is exposed to atmosphere surround the subject, may be a first exterior surface, as opposed to the portion of the epidermis layer that directly contacts the dermis layer. In a first optional embodiment step b (the cooling step) is omitted. In this optional embodiment, the method may comprise delivering an anesthetic to the first exterior surface in order to reduce any discomfort associated with the penetration of step c. In a second optional embodiment, step c (the penetrating step) is performed with a single needle rather than with a plurality of needles, and thus rather than extending from the first surface by a uniform distance into the patient, step c entails simply penetrating the surface with a needle, the needle extending from the first surface by a distance into the patient. In a third optional embodiment, in step d (the withdrawing and ejecting step), the material is ejected but the ejection does not necessarily occur while the needles are being withdrawn from the patient. Thus, in this optional embodiment, step d would recite that the material is ejected out of the needles and into the patient, and that the needles are withdrawn from the patient, but that the two events do not necessarily occur simultaneously. In a fourth optional embodiment, step e (the repeating step) is omitted, so that the patient necessarily receives only a single injection, however optionally receives multiple injections. In a fifth optional embodiment, step e further requires that additional material is delivered to the patient at the same location as the previous injection delivered material. In other words, the patient receives more than one injection at the same location on the patient, although at different times.

In methods of the present disclosure, including methods that include ejecting a material out of one or more needles and into a patient, the material to be delivered into the patent may be any of the materials identified herein, including the following specific embodiments: the material is a shear-sensitive material, which refers to a material such as some cellular materials which are harmed and become less efficacious upon being exposed to shear forces as are typically experienced when liquids are ejected from a typical syringe needle; the material comprises whole cells; the material comprises DSC cells; the material comprises adipose-derived mesenchymal stem cells; the material comprises platelet rich plasma; the material comprises fibroblasts; the material comprises adipocytes; the material comprises hyaluronic acid; the material comprises botulinus toxin; the material comprises growth factor(s); the material comprises glutathione; the material comprises melanocytes; the material comprises collagenase; the material comprises adipose tissue. The delivery may occur through any of the needles and needle arrays as identified herein, including the following specific embodiments: the material is ejected out of a plurality of needles selected from 9 to 16 needles; the plurality of needles are distributed over an area of about 1 $cm^2$; and the needles have a gauge selected from 18 to 32 gauge. In various embodiments, the needles can have a gauge of 18, 19, 20, 21, 22, 23, 24, 25, 26, or 27.

The delivery may be further characterized by any of the features as identified herein, including the following specific embodiments: the plurality of needles penetrate a distance selected from about 0.5 mm to about 5.0 mm below the first exterior surface; the plurality of needles penetrate a distance selected from about 2 cm to about 5 cm; the material is ejected into an epidermal layer of the subject; the material is ejected into a dermal layer of the subject; the material is ejected into a subcutis layer of the subject; the material is ejected into ligament of the subject; the material is ejected into a muscle tissue of the subject; the material is ejected into a tendon of the subject; the material is ejected into a scalp of the subject; the material is ejected into fascia of the subject; a total volume of material selected from about 50 μl to 90 μl is placed in the patient; each needle ejects a volume of material selected from about 50 μl to 90 μl into the patient; the needles penetrate the first surface at an angle of about 90 degrees, the angle defined by the place of the first surface and a longitudinal axis of a needle. The method may be further characterized in terms of the goal achieved by the method, including any of the goals identified herein, such as the following specific embodiments: the method is used to treat hair loss; the method is used to treat a chronic skin disorder; the method is used to lighten skin. Two or more of these specific embodiments may be combined in order to further characterize a method of the present disclosure.

In other optional embodiments, which may further characterize any of the elsewhere provided method embodiments of the present disclosure, the material is delivered only to the epidermis of the patient, or only to the dermis of the patient, or only to the subcutaneous fat layer of the patient. Due to the precision with which the dermal injector of the present invention can operate, a particular layer of skin can be targeted for selective material delivery. Alternatively, the material may optionally be delivered to an area underneath the skin, including tissue that resides directly or indirectly underneath the skin, or to a void that sits underneath the skin. The methods of the present disclosure may deliver any liquid material, including the materials identified elsewhere herein.

By incorporating electrical power and digital controls, the device of the present disclosure automates and simplifies the injection process. The presence of an optional touch screen as a component of the docketing station allows programmability for the delivery of precise quantities of material, at specific depths, through needles, optionally fine gauge needle. The delivery may be on a single plain or trailing through multi-plains as the needle retracts through the skin.

The device of the present disclosure provides a motorized injection device with programmable depth and volume, a built-in Peltier element for pre-injection anaesthetising, and interchangeable needle head configurations. It is designed to deliver a variety of injectable substances including cells, dermal fillers, drugs or biologics and deliver them intradermally (dermis), subcutaneously (fat) or intramuscularly (muscle) via a variety of needle configurations ranging from a single needle, to two needles, and including needle arrays such as a four needle array (2×2), a nine needle array (3×3), a 16 needle configuration (4×4), a 25 needle configuration (5×5), and a 36 needle configuration (6×6) on one head. The array need not have the same number of needles in each of the x and y directions, e.g., the array may be a 2×4 or 2×6 or 2×8 or 2×10 array, etc. The heads are interchangeable, i.e., a head on the handpiece can be substituted for a different head having different needles, and these interchangeable heads can be used to perform a variety of procedures, adjust surface area coverage and overall speed-up procedure times.

Benefits of the injector of the present disclosure include ease of handling, reduction or elimination of the need for local anesthetics, quicker procedure times, an expectation of enhanced intra- and inter-patient clinical results because of injection controls (e.g., the injection specialist is allowed to focus on product placement vs injection technique), and a significant expansion of the areas that can be injected due to the ability to conduct broad, shallow, and evenly-dispersed injections. The device provides for the delivery of a variety of injectables in a controlled, precise manner, removing the risks and uncertainties of injection outcomes currently resulting from manually operated, single-needle syringes.

Certain words and phrases used in the specification are set forth as follows. As used throughout this document, including the claims, the singular form "a", "an", and "the" include plural references unless indicated otherwise. For example, "a" needle includes one or more needles. Any of the features and elements described herein may be singular, e.g., a chamber may refer to one chamber and a handle may refer to one handle. The terms "include" and "comprise," as well as derivatives thereof, mean inclusion without limitation. The term "or," is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation, where such a device may be implemented in hardware, firmware, or software, or some combination of at least two of the same. The functionality associated with any particular controller may be centralized or distributed, whether locally or remotely. Other definitions of certain words and phrases are provided throughout this patent document. Those of ordinary skill in the art will understand that in many, if not most instances, such definitions apply to prior as well as future uses of such defined words and phrases.

As used in the present disclosure, the term "module" refers to an application specific integrated circuit (ASIC), an electronic circuit, a processor and a memory operative to execute one or more software or firmware programs, combinational logic circuitry, or other suitable components (hardware, software, or hardware and software) that provide the functionality described with respect to the module.

A processor (i.e., a processing unit), as used in the present disclosure, refers to one or more processing units individually, shared, or in a group, having one or more processing cores (e.g., execution units), including central processing units (CPUs), digital signal processors (DSPs), microprocessors, micro controllers, state machines, and the like that execute instructions. The processors interchangeably refer to any type of electronic control circuitry configured to execute programmed software instructions. The programmed instructions may be high-level software instructions, compiled software instructions, assembly-language software instructions, object code, binary code, micro-code, or the like. The programmed instructions may reside in internal or external memory or may be hard-coded as a state machine or set of control signals. According to methods and devices referenced herein, embodiments describe software executable by the processor and operable to execute certain ones of the method acts.

In the present disclosure, memory may be used in one configuration or another. As known by one skilled in the art, each memory comprises any combination of volatile and non-volatile computer-readable media for reading and writing. Volatile computer-readable media includes, for example, random access memory (RAM). Non-volatile computer-readable media includes, for example, read only memory (ROM), magnetic media such as a hard-disk, an optical disk drive, a flash memory device, a CD-ROM, and/or the like. In some cases, a particular memory is separated virtually or physically into separate areas, such as a first memory, a second memory, a third memory, etc. In these cases, it is understood that the different divisions of memory may be in different devices or embodied in a single memory. The memory may be configured to store data. In the alternative or in addition, the memory may be a non-transitory computer readable medium (CRM) wherein the CRM is configured to store instructions executable by a processor. The instructions may be stored individually or as groups of instructions in files. The files may include functions, services, libraries, and the like. The files may include one or more computer programs or may be part of a larger computer program. Alternatively or in addition, each file may include data or other computational support material useful to carry out the computing functions of the systems, methods, and apparatus described in the present disclosure.

Control unit 62 may further include operative software found in a conventional embedded device such as an operating system, software drivers to direct operations through the I/O circuitry, networking circuitry, and other peripheral component circuitry. In addition, control unit 62 may include operative application software such as network software for communicating with other computing devices, database software for building and maintaining databases, and task management software for distributing the communication and/or operational workload amongst various CPU's. In some cases, control unit 62 is a single hardware device having the hardware and software listed herein, and in other cases, control unit 62 is a networked collection of discrete hardware and software devices working together to execute the functions of the dermal injector. The conventional hardware and software of control unit 62 is not shown in FIG. 14 for simplicity.

Software stored in memory 66 may include a fully executable software program, a simple configuration data file, a link to additional directions, or any combination of known software types. When the control unit 62 updates software, the update may be small or large. For example, in some cases, control unit 62 downloads a small configuration data file, and in other cases, control unit 62 completely replaces all of the functional program instructions in memory 66 with a fresh version. In some cases, the software and data in memory 66 is encrypted, encoded, and/or otherwise compressed for reasons that include security, privacy, data transfer speed, data cost, or the like.

When so arranged as described herein, the control unit 62 is transformed from a generic and unspecific computing device to a combination device comprising hardware and software configured for a specific and particular purpose.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

Generally, unless otherwise indicated, the materials for making the invention and/or its components may be selected from appropriate materials such as metal, metallic alloys, ceramics, plastics, etc.

As described herein, for simplicity, a patient, clinician, or another human may in some cases be described in the context of the male gender. It is understood that a medical practitioner can be of any gender, and the terms "he," "his," "himself," and the like as used herein are to be interpreted broadly inclusive of all known gender definitions.

All of the U.S. patents, U.S. patent application publications, U.S. patent applications, foreign patents, foreign patent applications and non-patent publications referred to in this specification and/or listed in the Application Data Sheet, including but not limited to PCT Publication No. WO 2013/113121, are incorporated herein by reference, in their entirety. Such documents may be incorporated by reference for the purpose of describing and disclosing, for example, materials and methodologies described in the publications, which might be used in connection with the presently described invention. The publications discussed above and throughout the text are provided solely for their disclosure prior to the filing date of the present application. Nothing herein is to be construed as an admission that the inventors are not entitled to antedate any referenced publication by virtue of prior invention.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of delivering a liquid substance comprising cells into tissue, the method comprising placing the liquid substance into an injection device and then injecting the liquid substance from the injection device and into the tissue;
    wherein the injection device comprises a proximal end and a distal end, the distal end for introducing the liquid substance into a body of a subject, the injection device further comprising:
    a) an injector comprising at least one needle and a housing for the at least one needle;
    b) a cartridge comprising at least one chamber to hold the liquid substance, and a plunger which moves within the chamber to change a volume of the chamber; and
    c) a delivery mechanism to independently move the plunger and the at least one needle toward the distal end of the device, the delivery mechanism comprising means for adjusting the volume of the cartridge to inject the liquid substance through the at least one needle and an electromechanical drive device arranged to advance and retract the at least one needle, wherein the means for adjusting the volume of the cartridge and the electromechanical drive device are operable independently, so that the volume of the cartridge can be adjusted to inject the liquid substance through the at least one needle while the at least one needle is being retracted, the delivery mechanism comprising a distal drive that is movable relative to the proximal end of the injection device, a proximal drive that is stationary relative to the proximal end of the injection device and a threaded rod that joins the proximal and distal drives and the plunger;
    wherein the liquid substance is injected into the body while the at least one needle is being retracted.

2. A method of delivering a liquid substance comprising hyaluronic acid into tissue, the method comprising placing the liquid substance into an injection device and then injecting the liquid substance from the injection device and into the tissue;
    wherein the injection device comprises a proximal end and a distal end, the distal end for introducing a liquid substance into a body of a subject, the injection device further comprising:

a) an injector comprising at least one needle and a housing for the at least one needle;
b) a cartridge comprising at least one chamber to hold the liquid substance, and a plunger which moves within the chamber to change a volume of the chamber; and
c) a delivery mechanism to independently move the plunger and the at least one needle toward the distal end of the injection device, the delivery mechanism comprising means for adjusting the volume of the cartridge to inject the liquid substance through the needle and an electromechanical drive device arranged to advance and retract the at least one needle, wherein the means for adjusting the volume of the cartridge and the electromechanical drive device are operable independently, so that the volume of the cartridge can be adjusted to inject the liquid substance through the at least one needle while the at least one needle is being retracted, the delivery mechanism comprising a distal drive that is movable relative to the proximal end of the injection device, a proximal drive that is stationary relative to the proximal end of the injection device and a threaded rod that joins the proximal and distal drives and the plunger;
wherein the liquid substance is injected into the body while the at least one needle is being retracted.

* * * * *